United States Patent
Lian et al.

(10) Patent No.: US 11,661,413 B2
(45) Date of Patent: *May 30, 2023

(54) PYRAZOLE COMPOUNDS OR SALTS THEREOF, PREPARATION METHOD THEREFOR, HERBICIDAL COMPOSITION AND USE THEREOF

(71) Applicant: Qingdao Kingagroot Chemical Compounds Co., Ltd., Shandong (CN)

(72) Inventors: Lei Lian, Shandong (CN); Yurong Zheng, Shandong (CN); Song Li, Shandong (CN); Xuegang Peng, Shandong (CN); Tao Jin, Shandong (CN); Qi Cui, Shandong (CN)

(73) Assignee: QINGDAO KINGAGROOT CHEMICAL COMPOUNDS CO., LTD., Shandong (CN)

( * ) Notice: Subject to any disclaimer, the term of this patent is extended or adjusted under 35 U.S.C. 154(b) by 756 days.

This patent is subject to a terminal disclaimer.

(21) Appl. No.: 15/562,633

(22) PCT Filed: Mar. 4, 2016

(86) PCT No.: PCT/CN2016/075577
§ 371 (c)(1),
(2) Date: Sep. 28, 2017

(87) PCT Pub. No.: WO2017/113508
PCT Pub. Date: Jul. 6, 2017

(65) Prior Publication Data
US 2018/0086738 A1 Mar. 29, 2018

(30) Foreign Application Priority Data
Dec. 31, 2015 (CN) .......................... 201511030167.3

(51) Int. Cl.
*A01N 43/56* (2006.01)
*C07D 231/20* (2006.01)
(Continued)

(52) U.S. Cl.
CPC ........... *C07D 403/12* (2013.01); *A01N 25/00* (2013.01); *A01N 43/56* (2013.01); *C07C 22/04* (2013.01);
(Continued)

(58) Field of Classification Search
CPC ................ C07D 403/12; C07D 231/12; C07D 231/18; C07D 231/20; C07D 401/14;
(Continued)

(56) References Cited

U.S. PATENT DOCUMENTS 4,948,887 A 8/1990 Masatoshi et al.
5,013,659 A 5/1991 Bedbrook et al.
(Continued)

FOREIGN PATENT DOCUMENTS

CN 88101455 A 9/1988
CN 1224420 A 7/1999
(Continued)

OTHER PUBLICATIONS

U.S. Appl. No. 15/561,394, filed Sep. 2017, Lian et al.*
European Patent Office, Supplementary European Search Report issued in European Application No. 16880317.9 (dated Aug. 30, 2018).
(Continued)

*Primary Examiner* — John Pak
(74) *Attorney, Agent, or Firm* — Leydig, Voit & Mayer, Ltd.

(57) ABSTRACT

Disclosed are a pyrazole compound or a salt thereof, a preparation method therefor, a herbicidal composition and use thereof. The pyrazole compound or a salt thereof has a structure as shown in formula (I):

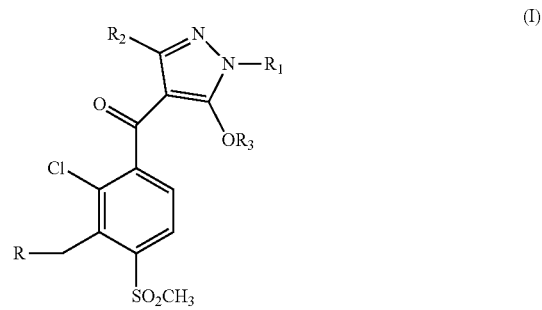

wherein, R represents

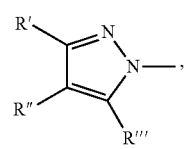

wherein, R', R", and R''' represent hydrogen, C1-C4 alkyl, C1-C4 halogenated alkyl, C1-C4 alkoxy or halogen, R', R", and R''' may be the same or different; $R_1$ represents C1-C3 alkyl; $R_2$ represents hydrogen or C1-C4 alkyl; $R_3$ represents hydrogen or C1-C6 alkyl, optionally substituted phenyl, optionally substituted pyridyl, optionally substituted alkenyl, optionally substituted alkynyl, C1-C6 alkyl carbonyl, C1-C6 alkoxyl carbonyl, C1-C6 alkyl carbonyl methyl, etc. A compound having a pyrazole structure not only has excellent herbicidal effect on barnyard grass, but also is safe to rice in post-emergence application. More surprisingly, it also has good control efficacy on barnyard grass resistant to major herbicides, such as penoxsulam, quinclorac, cyhalofop-butyl, propanil, etc.

19 Claims, No Drawings

(51) Int. Cl.
  *C07D 403/12* (2006.01)
  *C07C 22/04* (2006.01)
  *C07C 23/08* (2006.01)
  *A01N 25/00* (2006.01)
  *C07D 401/14* (2006.01)
  *C07D 231/12* (2006.01)
  *C07D 231/18* (2006.01)
  *C07D 403/10* (2006.01)

(52) U.S. Cl.
  CPC ............ *C07C 23/08* (2013.01); *C07D 231/12* (2013.01); *C07D 231/18* (2013.01); *C07D 231/20* (2013.01); *C07D 401/14* (2013.01); *C07D 403/10* (2013.01)

(58) Field of Classification Search
  CPC ....... C07D 403/10; C07C 22/04; C07C 23/08; A01N 25/00; A01N 43/56
  USPC ................................................. 504/219, 282
  See application file for complete search history.

(56) References Cited

U.S. PATENT DOCUMENTS

| | | | |
|---|---|---|---|
| 5,824,802 | A | 10/1998 | Benko et al. |
| 5,846,907 | A * | 12/1998 | von Deyn .............. A01N 43/56 504/221 |
| 6,147,031 | A | 11/2000 | Adachi et al. |
| 6,156,702 | A | 12/2000 | Engel et al. |
| 6,165,944 | A | 12/2000 | von Deyn et al. |
| 6,207,618 | B1 * | 3/2001 | Engel ..................... A01N 43/56 504/130 |
| 6,376,429 | B1 | 4/2002 | Van Almsick et al. |
| 6,432,881 | B1 | 8/2002 | Engel et al. |
| 6,448,201 | B1 | 9/2002 | Seitz et al. |
| 6,831,039 | B1 | 12/2004 | Neidlein et al. |
| 7,189,679 | B2 | 3/2007 | Schmitt et al. |
| 2005/0119129 | A1 | 6/2005 | Schwarz et al. |
| 2005/0153958 | A1 | 7/2005 | Hoischen et al. |
| 2011/0144345 | A1 | 6/2011 | Tamai et al. |

FOREIGN PATENT DOCUMENTS

| | | |
|---|---|---|
| CN | 1269800 A | 10/2000 |
| CN | 1278259 A | 12/2000 |
| CN | 1332738 A | 1/2002 |
| CN | 1938277 A | 3/2007 |
| CN | 103980202 A | 8/2014 |
| DE | 19846792 A1 | 4/2000 |
| EP | 0131624 A1 | 1/1985 |
| EP | 0142924 A2 | 5/1985 |
| EP | 0193259 A1 | 9/1986 |
| EP | 0221044 A1 | 5/1987 |
| EP | 0242236 A1 | 10/1987 |
| EP | 0242246 A1 | 10/1987 |
| EP | 0257993 A2 | 3/1988 |
| EP | 1031573 A1 | 8/2000 |
| EP | 1135388 A2 | 9/2001 |
| EP | 2106697 A1 | 10/2009 |
| JP | S63-122673 A | 5/1988 |
| JP | H11-509202 A | 8/1999 |
| JP | 2001-514171 A | 9/2001 |
| JP | 2001-514172 A | 9/2001 |
| JP | 2003-513081 A | 4/2003 |
| JP | 2005-517736 A | 6/2005 |
| JP | 2005-519113 A | 6/2005 |
| JP | 2008-081406 A | 4/2008 |
| RU | 2055836 C1 | 3/1996 |
| WO | WO 84/02919 A1 | 8/1984 |
| WO | WO 91/13972 A1 | 9/1991 |
| WO | WO 91/19806 A1 | 12/1991 |
| WO | WO 92/00377 A1 | 1/1992 |
| WO | WO 92/11376 A1 | 7/1992 |
| WO | WO 92/14827 A1 | 9/1992 |
| WO | WO 97/03045 A1 | 1/1997 |
| WO | WO 98/42648 A1 | 10/1998 |
| WO | WO 00/03993 A1 | 1/2000 |
| WO | WO 2010/016230 A1 | 2/2010 |

OTHER PUBLICATIONS

"Molecular Cloning: A Laboratory Manual," 4th Edition, Eds. Michael R. Green & Joseph Sambrook, *Cold Spring Harbor Laboratory Press*, Cold Spring Harbor, NY, 2012 (Table of Contents and Preface).
State Intellectual Property Office of the People's Republic of China, International Search Report and Written Opinion issued in International Application No. PCT/CN2016/075577 (dated Sep. 14, 2016).
Federal Service on Intellectual Property, Search Report issued in Russian Application No. 2018111723 (Search completed Dec. 20, 2019).
Federal Service on Intellectual Property, Official Action issued in Russian Application No. 2018111723 (dated Feb. 15, 2019).
State Intellectual Property Office of People's Republic of China, First Office Action in Chinese Application No. 201511030167.3 (dated Jul. 5, 2016).
State Intellectual Property Office of People's Republic of China, Second Office Action in Chinese Application No. 201511030167.3 (dated Oct. 10, 2016).
U.S. Appl. No. 15/561,394, filed Sep. 25, 2017.
African Regional Intellectual Property Organization, Search Report issued in African Patent Application No. AP/P/2017/010271 (dated Jan. 9, 2020).
Intellectual Property of India, First Examination Report issued in Indian Patent Application No. 201747035236 (dated Jun. 17, 2019).
IP Australian, Examination Report No. 1 issued in Australian Patent Application No. 2016382562 (dated Jun. 28, 2018).
Russian Patent Office, Official Action issued in Russian Application No. 2018110616 (dated Dec. 3, 2018).
Russian Patent Office, Search Report issued in Russian Application No. 2018110616 (dated Dec. 3, 2018).

* cited by examiner

PYRAZOLE COMPOUNDS OR SALTS THEREOF, PREPARATION METHOD THEREFOR, HERBICIDAL COMPOSITION AND USE THEREOF

TECHNICAL FIELD

This patent application is the U.S. national phase of International Application No. PCT/CN2016/075577, filed on Mar. 4, 2016, which claims the benefit of Chinese Patent Application No. 201511030167.3, filed Dec. 31, 2015, the disclosures of which are incorporated herein by reference in their entireties for all purposes.

The present invention relates to the technical field of pesticides, particularly relates to a pyrazole compound or a salt thereof, a preparation method therefor, a herbicidal composition and use thereof.

BACKGROUND TECHNOLOGY

Barnyard grass is the most important weed in rice field, especially with the development of direct seeding technology, the management of barnyard grass has become the key to increase growing returns. A large number of barnyard grass herbicides have been developed, for example ALS inhibitors (for example, penoxsulam, triafamone, etc.) and ACCase inhibitors (for example, cyhalofop-butyl, metamifop, fenoxaprop-p-ethyl, clefoxidim, etc.), however, with the mass application of these herbicides, the resistance of barnyard grass has become increasingly serious. It is reported that, currently, a lot of barnyard grass biotypes have evolved resistant to the main barnyard grass herbicides. Therefor, it is urgent to develop a herbicide with no cross-resistance to the current mainstream barnyard grass herbicides.

CONTENTS OF THE INVENTION

In order to resolve the above problem in the prior art, the present invention provides a pyrazole compound or a salt thereof, a preparation method therefor, a herbicidal composition and use thereof. It is surprisingly to find that the pyrazole compound has not only good effect against barnyard grass, but also is safe to rice when applied after sprout. More surprisingly, it exhibits excellent effect on barnyard grass resistant to main herbicides, such as penoxsulam, quinclorac, cyhalofop-butyl and propanil, etc.

In order to achieve the above objective, the present invention provides the following technical solution:

A pyrazole compound of formula (I) or a salt thereof:

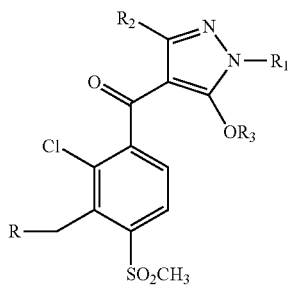

wherein,
R represent

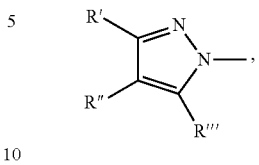

wherein R', R", and R'" represent hydrogen, C1-C4 alkyl, C1-C4 halogenated alkyl, C1-C4 alkoxyl or halogen, R', R", R'" may be the same or different;
$R_1$ represents C1-C3 alkyl;
$R_2$ represents hydrogen or C1-C4 alkyl;
$R_3$ represents hydrogen or C1-C6 alkyl, optionally substituted phenyl, optionally substituted pyridyl, optionally substituted alkenyl, optionally substituted alkynyl, C1-C6 alkyl carbonyl, C1-C6 alkoxyl carbonyl, C1-C6 alkyl carbonyl methyl, C1-C6 alkoxyl carbonyl methyl, C1-C4 alkyl sulfonyl, C1-C4 halogenated alkyl sulfonyl, phenylsulfonyl or phenylsulfonyl substituted by alkyl, alkoxyl or halogen, benzoyl or benzoyl substituted by halogen, nitro, alkyl or alkoxyl, phenoxyl carbonyl or phenoxyl carbonyl substituted by halogen, nitro, alkyl or alkoxyl, benzoyl methyl or benzoyl methyl substituted by halogen, nitro, alkyl or alkoxyl, phenoxyl carbonyl methyl or phenoxyl carbonyl methyl substituted by halogen, nitro, alkyl or alkoxyl.
Preferably, R', R", and R'" represent hydrogen, methyl, methoxyl, fluoro methyl or chlorine, wherein, R', R", R'" may be the same or different.
$R_1$ represents methyl, ethyl or isopropyl;
$R_2$ represents hydrogen, methyl, ethyl or cyclopropyl;
$R_3$ represents hydrogen or C1-C6 alkyl, optionally substituted phenyl, optionally substituted pyridyl, optionally substituted alkenyl, optionally substituted alkynyl, C1-C6 alkyl carbonyl, C1-C6 alkoxyl carbonyl, C1-C6 alkyl carbonyl methyl, C1-C6 alkoxyl carbonyl methyl, C1-C4 alkyl sulfonyl, C1-C4 halogenated alkyl sulfonyl, phenylsulfonyl or phenylsulfonyl substituted by alkyl, alkoxyl or halogen, benzoyl or benzoyl substituted by halogen, nitro, alkyl or alkoxyl, phenoxyl carbonyl or phenoxyl carbonyl substituted by halogen, nitro, alkyl or alkoxyl, benzoyl methyl or benzoyl methyl substituted by halogen, nitro, alkyl or alkoxyl, phenoxyl carbonyl methyl or phenoxyl carbonyl methyl substituted by halogen, nitro, alkyl or alkoxyl.

A compound of formula (III):

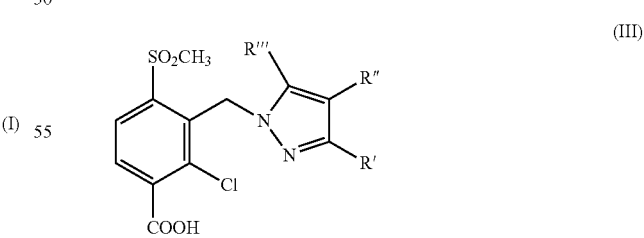

wherein,
R', R", and R'" represent hydrogen, C1-C4 alkyl, C1-C4 halogenated alkyl, C1-C4 alkoxyl or halogen; R', R", and R'" may be the same or different.
Preferably, R', R", and R'" represent hydrogen, methyl, methoxyl, or chlorine; R', R", and R'" may be the same or different.

A compound of formula (V):

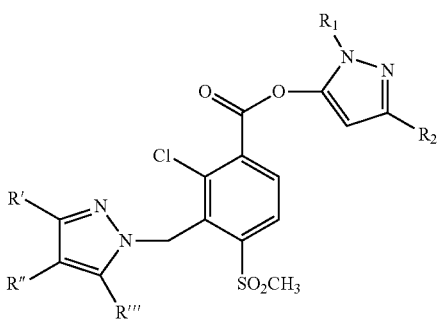

wherein,
R', R", and R'" represent hydrogen, C1-C4 alkyl, C1-C4 halogenated alkyl, C1-C4 alkoxyl or halogen; R', R", and R'" may be the same or different.
$R_1$ represents C1-C3 alkyl;
$R_2$ represents hydrogen or C1-C4 alkyl;
Preferably, R', R", and R'" represent hydrogen, methyl, methoxyl, or chlorine; R', R", and R'" may be the same or different.
$R_1$ represents methyl, ethyl or isopropyl;
$R_2$ represents hydrogen, methyl, ethyl or cyclopropyl;

In the definition of the above compound, the terms used, either alone or in combine with other terms, represent the following groups:

Halogen refers to fluorine, chlorine, bromine, or iodine;
Alkyl refers to linear chain alkyl or branch chain alkyl;
Halogenated alkyl refers to a linear or branch alkyl with all or part of the hydrogen atoms substituted by halogen atoms;
Alkoxyl refers to a functional group formed by linking an alkyl with an oxygen.

If necessary, the compound of formula (I) can form a corresponding salt thereof through conventional methods. The salt could be in any forms, provided that it is agriculturally acceptable, for example, an alkali metal salt (e.g. a sodium salt or a potassium salt), an alkaline-earth metal salt (e.g. a magnesium salt or a calcium salt), or an ammonium salt (e.g. a dimethylamine salt or a triethylamine salt).

The compound of the present invention may exist in a form of one or multiple stereoisomer. The stereoisomer comprises an enantiomer, a diastereoisomer and a geometric isomer. All of these stereoisomers and mixture thereof are within the scope of the present invention.

Also disclosed in the present invention is a method for preparing the pyrazole compound of formula (I) or the salt thereof, wherein 2-chloro-3-bromomethyl-4-methylsulfonyl benzoic acid is used as a starting material.

Also disclosed is a method for preparing the pyrazole compound of formula (I-1) or the salt thereof, comprising the following steps:

(1) the compound 2-chloro-3-bromomethyl-4-methylsulfonyl benzoic acid is reacted with a compound of formula (II) to obtain a compound of formula (III);

(2) the compound of formula (III) is reacted with a compound of formula (IV) to obtain a compound of formula (V);

(3) the compound of formula (V) is subjected to a rearrangement reaction to afford a compound of formula (I) with hydrogen as $R_3$ (namely formula (I-1)); the pyrazole compound of formula (I-1) or the salt thereof may be prepared via the following reaction route:

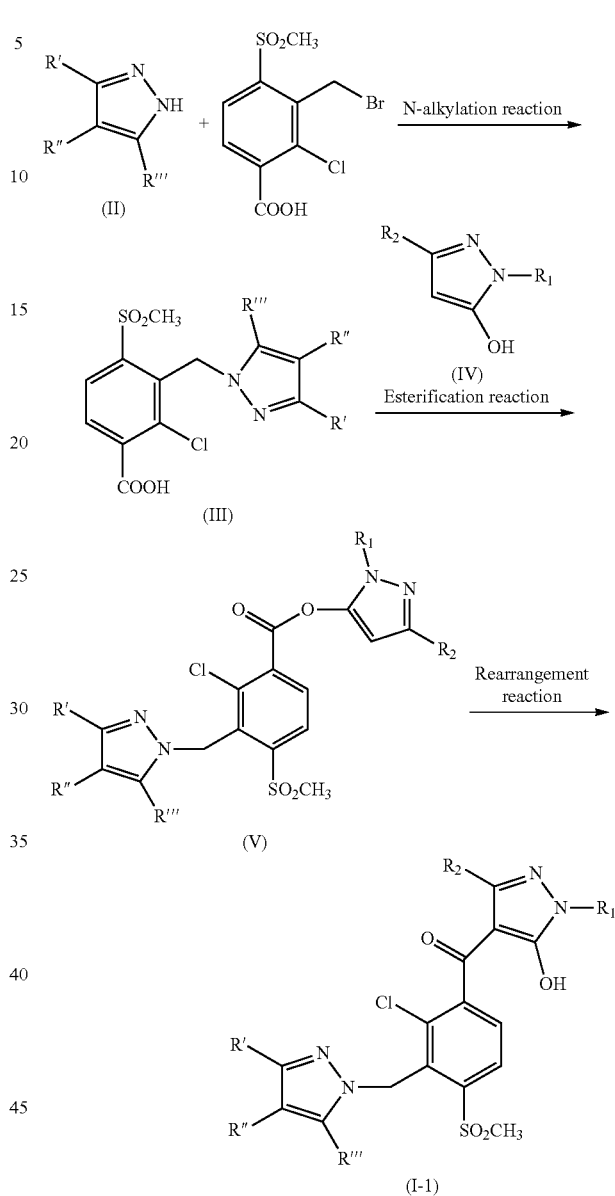

The above mentioned alkylation reaction needs to be conducted in the presence of a solvent. The solvent used is inert to the reaction. Such solvent is generally an aprotic polar solvent, such as acetonitrile, DMF, DMSO or a mixed solvent, preferably acetonitrile.

The above mentioned N-alkylation reaction needs to be conducted in the presence of an alkali, which is generally a metal hydride, such as sodium hydride, potassium hydride, preferably sodium hydride.

The reaction temperature of the above mentioned N-alkylation reaction is generally −10-30° C., preferably 0-10° C.; the reaction time is 0.5-48 hours, preferably 1-12 hours.

In order to reduce the reaction time and increase esterification reaction rate, the above mentioned esterification reaction generally comprises two steps: first, the compound of formula (III) is converted to its corresponding acyl chloride; second, the acyl chloride is reacted with the compound of formula (IV) to obtain the compound of formula (V). That is, the compound of formula (V) is obtained by reacting a compound of formula (III') with the compound of formula (IV). The compound of formula (III') is as follows:

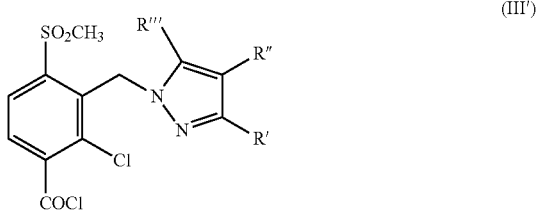

wherein, R', R", R''' are defined as above.

A compound of formula (III) can be converted to a compound of formula (III') through the following route:

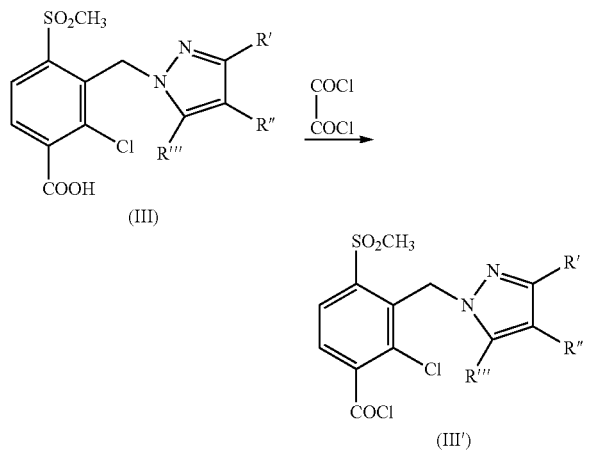

wherein, R', R", R''' are defined as above.

The above mentioned esterification reaction needs to be conducted in the presence of a solvent. The solvent used is inert to the reaction. The solvent is generally an aprotic solvent, which is either polar or non-polar. For example, acetonitrile, methylbenzene, dimethylbenzene, dichloromethane, dichloroethane, tetrahydrofuran, or acetone, etc., preferably 1,2-dichloroethane.

The second step of the esterification reaction needs to be conducted in the presence of a deacid reagent, the deacid reagent used is a common alkali, either inorganic or organic. One or more of such alkali could be selected for use from carbonates (e.g. sodium carbonate, potassium carbonate), bicarbonates (e.g. sodium bicarbonate, potassium bicarbonate), amines (e.g. dimethylamine, triethylamine, N,N-diisopropylethylamine), and pyridines (e.g. pyridine, 4-dimethylaminopyridine), preferably triethylamine.

The reaction temperature of the esterification reaction is generally between −10 to 50° C., preferably 0 to 10° C.; the reaction time is between 0.5 to 24 hours, preferably 1 to 6 hours.

The rearrangement reaction is conducted in the reaction system of the esterification reaction. Or rather, the reaction liquid could be used directly for the rearrangement reaction without any workup after the esterification reaction. Hence, the solvent needed for the rearrangement reaction is the same with the above mentioned esterification reaction.

The above mentioned rearrangement reaction comprises two steps. Firstly, rearrange of the compound of formula (V); Secondly, pH regulation of the system. Namely, a required amount of water is added into the system after the first step and the system is regulated to acidic. Generally, an acid for pH adjustment is hydrochloric acid.

The reaction temperature of the first step of the rearrangement reaction is generally between 0 to 100° C., preferably 40 to 60° C.; the reaction time is 0.5 to 24 hours, preferably 1 to 6 hours. The reaction temperature of the pH regulation step is 10 to 50° C., preferably 10 to 25° C.

If necessary, an appropriate amount of catalyst is added before the rearrangement reaction. In the present invention, the catalyst is preferable acetone cyanohydrin.

The compound of formula (III) and formula (V) related in the route is novel intermediates and can be used to prepare the compound of the present invention.

In order to increase diversity of the compound, the structure of the compound of formula (I) with hydrogen as $R_3$ (i.e. formula (I-1)) is modified accordingly through molecular designing, thus the compound of formula (I) with non-hydrogen as $R_3$ (i.e. formula (I')) is derived. A pyrazole compound of formula (I') related to the present invention is prepared by reacting the compound of formula (I-1) with a compound of formula (VI). A reaction route is as follows:

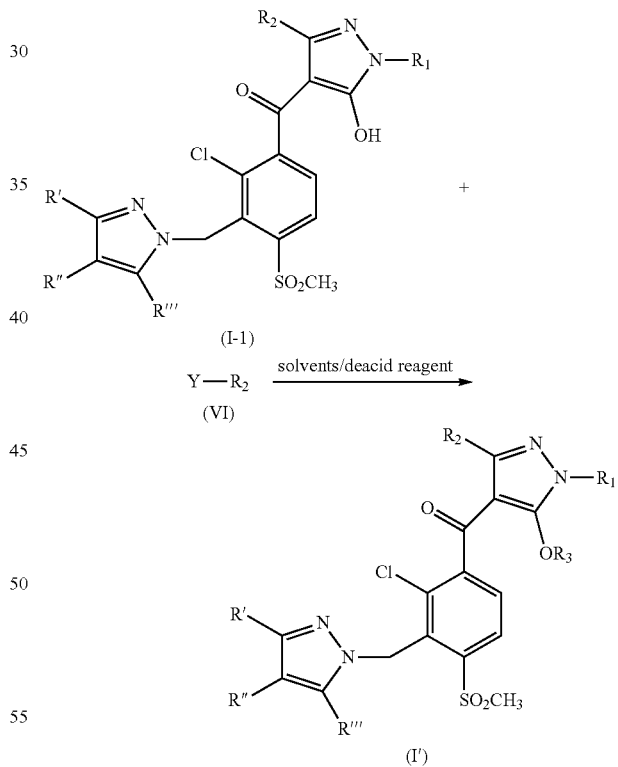

wherein, Y represents halogen, preferably chlorine, bromine or iodine.

The preparation of the above mentioned formula (I') should be conducted in the presence of a solvent. The solvent used should be inert to the reaction. Such solvent is generally a non-protonic solvent, either polar or non-polar, for example, acetonitrile, methylbenzene, dimethylbenzene, dichloromethane, dichloroethane, tetrahydrofuran or acetone, preferably acetonitrile or dichloromethane.

The preparation method of formula (I') needs to be conducted in the presence of a deacid reagent; the deacid reagent used is a common alkali, either inorganic or organic. One or more of such alkalis could be selected for use from carbonates (e.g. sodium carbonate, potassium carbonate), bicarbonates (e.g. sodium bicarbonate, potassium bicarbonate), amines (e.g. dimethylamine, triethylamine, N,N-diisopropylethylamine), and pyridines (e.g. pyridine, 4-dimethylaminopyridine), preferably triethylamine or potassium carbonate.

The reaction temperature for the preparation of formula (I') is usually between −10 to 50° C., preferably 0 to 20° C.; the reaction time is usually 0.1 to 12 hours, preferably 0.5 to 3 hours.

Also disclosed is a herbicidal composition which comprises a herbicidally effective amount of at least one pyrazole compound or the salt thereof.

The herbicidal composition also comprises a preparation auxiliary.

Also disclosed is a method for controlling a harmful plant, which comprises a step of applying a herbicidally effective amount of at least one pyrazole compound or the salt thereof or the herbicidal composition to the plant or an area with the harmful plant.

Use of at least one pyrazole compound or the salt thereof or the herbicidal composition in controlling a harmful plant, preferably, the pyrazole compound or the salt thereof is applied to control the harmful plant in a desirable crop, preferably, the desirable crop is a genetically modified crop or a crop treated by a genome editing technique.

The compounds of the formula (I) according to the invention have an outstanding herbicidal activity against a broad spectrum of economically important monocotyledonous and dicotyledonous harmful plants. The active compounds also act efficiently on perennial weeds which produce shoots from rhizomes, root stocks or other perennial organs and which are difficult to control. In this context, it is generally immaterial whether the substances are applied pre-sowing, pre-emergence or post-emergence. Specifically, examples may be mentioned of some representatives of the monocotyledonous and dicotyledonous weed flora which can be controlled by the compounds according to the invention, without these being a restriction to certain species. Examples of weed species on which the active compounds act efficiently are, from amongst the monocotyledons, *Avena, Lolium, Alopecurus, Phalaris, Echinochloa, Digitaria, Setaria* and also *Cyperus* species from the annual sector and from amongst the perennial species *Agropyron, Cynodon, Imperata* and *Sorghum*, and also perennial *Cyperus* species.

In the case of the dicotyledonous weed species, the spectrum of action extends to species such as, for example, *Galium, Viola, Veronica, Lamium, Stellaria, Amaranthus, Sinapis, Ipomoea, Sida, Matricaria* and *Abutilon* from amongst the annuals, and *Convolvulus, Cirsium, Rumex* and *Artemisia* in the case of the perennial weeds. The active compounds according to the invention also effect outstanding control of harmful plants which occur under the specific conditions of rice growing such as, for example, *Echinochloa, Sagittaria, Alisma, Eleocharis, Scirpus* and *Cyperus*. If the compounds according to the invention are applied to the soil surface prior to germination, then the weed seedlings are either prevented completely from emerging, or the weeds grow until they have reached the cotyledon stage but then their growth stops, and, eventually, after three to four weeks have elapsed, they die completely. If the compounds according to the invention are applied to the soil surface prior to germination, then the weed seedlings are either prevented completely from emerging, or the weeds grow until they have reached the cotyledon stage but then their growth stops, and, eventually, after three to four weeks have elapsed, they die completely. In particular, the compounds according to the invention exhibit excellent activity against *Apera spica venti, Chenopodium album, Lamium purpureum, Polygonum convulvulus, Stellaria media, Veronica hederifolia, Veronica persica, Viola tricolor* and against *Amaranthus, Galium* and *Kochia* species.

Although the compounds according to the invention have an excellent herbicidal activity against monocotyledonous and dicotyledonous weeds, crop plants of economically important crops such as, for example, wheat, barley, rye, rice, corn, sugarbeet, cotton and soya, are not damaged at all, or only to a negligible extent. In particular, they have excellent compatibility in cereals, such as wheat, barley and corn, in particular wheat. For these reasons, the present compounds are highly suitable for selectively controlling undesired plant growth in plantings for agricultural use or in plantings of ornamentals.

Owing to their herbicidal properties, these active compounds can also be employed for controlling harmful plants in crops of known or still to be developed genetically engineered plants. The transgenic plants generally have particularly advantageous properties, for example resistance to certain pesticides, in particular certain herbicides, resistance to plant diseases or causative organisms of plant diseases, such as certain insects or microorganisms such as fungi, bacteria or viruses. Other particular properties relate, for example, to the quantity, quality, storage-stability, composition and to specific ingredients of the harvested product. Thus, transgenic plants having an increased starch content or a modified quality of the starch or those having a different fatty acid composition of the harvested produce are known.

The use of the compounds of the formula (I) according to the invention or their salts in economically important transgenic crops of useful and ornamental plants, for example of cereal, such as wheat, barley, rye, oats, millet, rice, maniok and corn, or else in crops of sugarbeet, cotton, soya, rapeseed, potato, tomato, pea and other vegetable species is preferred. The compounds of the formula (I) can preferably be used as herbicides in crops of useful plants which are resistant or which have been made resistant by genetic engineering toward the phytotoxic effects of the herbicides.

Conventional ways for preparing novel plants which have modified properties compared to known plants comprise, for example, traditional breeding methods and the generation of mutants. Alternatively, novel plants having modified properties can be generated with the aid of genetic engineering methods (see, for example, EP-A 0 221 044, EP-A 0 131 624). For example, there have been described several cases of genetically engineered changes in crop plants in order to modify the starch synthesized in the plants (for example WO 92/11376, WO 92/14827, WO 91/19806), transgenic crop plants which are resistant to certain herbicides of the glufosinate- (cf., for example, EP-A 0 242 236, EP-A 0 242 246) or glyphosate-type (WO 92/00377), or of the sulfonylurea-type (EP-A 0 257 993, U.S. Pat. No. 5,013,659), transgenic crop plants, for example cotton, having the ability to produce *Bacillus thuringiensis* toxins (Bt toxins) which impart resistance to certain pests to the plants (EP-A 0 142 924, EP-A 0 193 259), transgenic crop plants having a modified fatty acid composition (WO 91/13972).

Numerous molecular biological techniques which allow the preparation of novel transgenic plants having modified properties are known in principle; see, for example, Sambrook et al., 1989, Molecular Cloning, A Laboratory Manual, 2nd ed. Cold Spring Harbor Laboratory Press, Cold Spring Harbor, N.Y.; or Winnacker "Gene und Klone" [Genes and Clones], VCH Weinheim, 2nd edition 1996, or Christou, "Trends in Plant Science" 1 (1996) 423-431). In order to carry out such genetic engineering manipulations, it is possible to introduce nucleic acid molecules into plasmids which allow a mutagenesis or a change in the sequence to occur by recombination of DNA sequences. Using the abovementioned standard processes it is possible, for example, to exchange bases, to remove partial sequences or to add natural or synthetic sequences. To link the DNA fragments with each other, it is possible to attach adaptors or linkers to the fragments.

Plant cells having a reduced activity of a gene product can be prepared, for example, by expressing at least one appropriate antisense-RNA, a sense-RNA to achieve a cosuppression effect, or by expressing at least one appropriately constructed ribozyme which specifically cleaves transcripts of the abovementioned gene product.

To this end it is possible to employ both DNA molecules which comprise the entire coding sequence of a gene product including any flanking sequences that may be present, and DNA molecules which comprise only parts of the coding sequence, it being necessary for these parts to be long enough to cause an antisense effect in the cells. It is also possible to use DNA sequences which have a high degree of homology to the coding sequences of a gene product but which are not entirely identical.

When expressing nucleic acid molecules in plants, the synthesized protein can be localized in any desired compartment of the plant cells. However, to achieve localization in a certain compartment, it is, for example, possible to link the coding region with DNA sequences which ensure localization in a certain compartment. Such sequences are known to the person skilled in the art (see, for example, Braun et al., EMBO J. 11 (1992), 3219-3227; Wolter et al., Proc. Natl. Acad. Sci. USA 85 (1988), 846-850; Sonnewald et al., Plant J. 1 (1991), 95-106).

The transgenic plant cells can be regenerated to whole plants using known techniques. The transgenic plants can in principle be plants of any desired plant species, i.e. both monocotyledonous and dicotyledonous plants. In this manner, it is possible to obtain transgenic plants which have modified properties by overexpression, suppression or inhibition of homologous (=natural) genes or gene sequences or by expression of heterologous (=foreign) genes or gene sequences.

When using the active compounds according to the invention in transgenic crops, in addition to the effects against harmful plants which can be observed in other crops, there are frequently effects which are specific for the application in the respective transgenic crop, for example a modified or specifically broadened spectrum of weeds which can be controlled, modified application rates which can be used for the application, preferably good combinability with the herbicides to which the transgenic crops are resistant, and an effect on the growth and the yield of the transgenic crop plants. The invention therefore also provides for the use of the compounds according to the invention as herbicides for controlling harmful plants in transgenic crop plants.

In addition, the substances according to the invention have outstanding growth-regulating properties in crop plants. They engage in the plant metabolism in a regulating manner and can this be employed for the targeted control of plant constituents and for facilitating harvesting, for example by provoking desiccation and stunted growth. Furthermore, they are also suitable for generally regulating and inhibiting undesirable vegetative growth, without destroying the plants in the process. Inhibition of vegetative growth plays an important role in many monocotyledon and dicotyledon crops because lodging can be reduced hereby, or prevented completely.

The compounds according to the invention can be applied in the customary formulations in the form of wettable powders, emulsifiable concentrates, sprayable solutions, dusts or granules. The invention therefore also provides herbicidal compositions comprising compounds of the formula (I). The compounds of the formula (I) can be formulated in various ways depending on the prevailing biological and/or chemico-physical parameters. Examples of suitable formulation options are: wettable powders (WP), water-soluble powders (SP), water-soluble concentrates, emulsifiable concentrates (EC), emulsions (EW), such as oil-in-water and water-in-oil emulsions, sprayable solutions, suspension concentrates (SC), oil- or water-based dispersions, oil-miscible solutions, dusts (DP), capsule suspensions (CS), seed-dressing compositions, granules for broadcasting and soil application, granules (GR) in the form of microgranules, spray granules, coating granules and adsorption granules, water-dispersible granules (WG), water-soluble granules (SG), ULV formulations, microcapsules and waxes. These individual formulation types are known in principle and are described, for example, in Winnacker-Kuhler, "Chemische Technologie" [Chemical Technology], Volume 7, C. Hauser Verlag Munich, 4th. Edition 1986; Wade van Valkenburg, "Pesticide Formulations", Marcel Dekker, N.Y., 1973; K. Martens, "Spray Drying" Handbook, 3rd Ed. 1979, G. Goodwin Ltd. London.

The necessary formulation auxiliaries, such as inert materials, surfactants, solvents and other additives, are likewise known and are described, for example, in Watkins, "Handbook of Insecticide Dust Diluents and Carriers", 2nd Ed., Darland Books, Caldwell N.J., H. v. Olphen, "Introduction to Clay Colloid Chemistry"; 2nd Ed., J. Wiley & Sons, N.Y.; C. Marsden, "Solvents Guide"; 2nd Ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schonfeldt, "Grenzflchenaktive thylenoxidaddukte" [Surface-active ethylene oxide adducts], Wiss. Verlagsgesell, Stuttgart 1976; Winnacker-Kuchler, "Chemische Technologie" [Chemical Technology], Volume 7, C. Hauser Verlag Munich, 4th Edition 1986.

Wettable powders are preparations which are uniformly dispersible in water and which contain, in addition to the active compound and as well as a diluent or inert substance, surfactants of ionic and/or nonionic type (wetting agents, dispersants), for example polyethoxylated alkyl phenols, polyethoxylated fatty alcohols, polyethoxylated fatty amines, fatty alcohol polyglycol ethersulfates, alkanesulfonates, alkylbenzenesulfonates, sodium ligninsulfonate, sodium 2,2'-dinaphthylmethane-6,6'-disulfonate, sodium dibutyi-naphthalenesulfona-te or else sodium oleoylmethyltaurinate. To prepare the wettable powders, the herbicidally active compounds are finely ground, for example in customary apparatus such as hammer mills, fan mills and air-jet mills, and are mixed simultaneously or subsequently with the formulation auxiliaries.

Emulsifiable concentrates are prepared by dissolving the active compound in an organic solvent, for example butanol, cyclohexanone, dimethylformamide, xylene or else relatively high-boiling aromatic compounds or hydrocarbons or mixtures of the solvents, with the addition of one or more surfactants of ionic and/or nonionic type (emulsifiers). Examples of emulsifiers which can be used are calcium alkylarylsulfonates, such as Ca dodecylbenzenesulfonate, or nonionic emulsifiers, such as fatty acid polyglycol esters, alkylaryl polyglycol ethers, fatty alcohol polyglycol ethers, propylene oxide-ethylene oxide condensation products, alkyl polyethers, sorbitan esters, for example sorbitan fatty acid esters or polyoxyethylene sorbitan esters, for example polyoxyethylene sorbitan fatty acid esters.

Dusts are obtained by grinding the active compound with finely divided solid substances, for example talc, natural clays, such as kaolin, bentonite and pyrophyllite, or diatomaceous earth. Suspension concentrates can be water- or oil-based. They can be prepared, for example, by wet milling using commercially customary bead mills, with or without the addition of surfactants as already mentioned above, for example, in the case of the other formulation types.

Emulsions, for example oil-in-water emulsions (EW), can be prepared for example by means of stirrers, colloid mills and/or static mixers using aqueous organic solvents and, if desired, surfactants as already mentioned above, for example, in the case of the other formulation types.

Granules can be prepared either by spraying the active compound onto adsorptive, granulated inert material or by applying active-compound concentrates to the surface of carriers such as sand, kaolinites or granulated inert material, by means of adhesive binders, for example polyvinyl alcohol, sodium polyacrylate or else mineral oils. Suitable active compounds can also be granulated in the manner which is customary for the preparation of fertilizer granules, if desired as a mixture with fertilizers. Water-dispersible granules are generally prepared by the customary processes, such as spray-drying, fluidized-bed granulation, disk granulation, mixing using high-speed mixers, and extrusion without solid inert material.

For the preparation of disk, fluidized-bed, extruder and spray granules, see for example processes in "Spray-Drying Handbook" 3rd ed. 1979, G. Goodwin Ltd., London; J. E. Browning, "Agglomeration", Chemical and Engineering 1967, pages 147 ff.; "Perry's Chemical Engineer's Handbook", 5th Ed., McGraw-Hill, New York 1973, pp. 8-57. For further details on the formulation of crop protection products, see for example G. C. Klingman, "Weed Control as a Science", John Wiley and Sons Inc., New York, 1961, pages 81-96 and J. D. Freyer, S. A. Evans, "Weed Control Handbook", 5th Ed., Blackwell Scientific Publications, Oxford, 1968, pages 101-103.

The agrochemical formulations generally contain from 0.1 to 99% by weight, in particular from 0.1 to 95% by weight, of active compound of the formula (I). In wettable powders the concentration of active compound is, for example, from about 10 to 90% by weight, the remainder to 100% by weight consisting of customary formulation constituents. In emulsifiable concentrates the concentration of active compound can be from about 1 to 90%, preferably from 5 to 80%, by weight. Formulations in the form of dusts contain from 1 to 30% by weight of active compound, preferably most commonly from 5 to 20% by weight of active compound, while sprayable solutions contain from about 0.05 to 80%, preferably from 2 to 50%, by weight of active compound. In the case of water-dispersible granules the content of active compound depends partly on whether the active compound is in liquid or solid form and on the granulation auxiliaries, fillers, etc. that are used. In water-dispersible granules the content of active compound, for example, is between 1 and 95% by weight, preferably between 10 and 80% by weight.

In addition, said formulations of active compound may comprise the tackifiers, wetting agents, dispersants, emulsifiers, penetrants, preservatives, antifreeze agents, solvents, fillers, carriers, colorants, antifoams, evaporation inhibitors and pH and viscosity regulators which are customary in each case.

Based on these formulations it is also possible to produce combinations with other pesticidally active substances, for example insecticides, acaricides, herbicides and fungicides, and also with safeners, fertilizers and/or growth regulators, for example in the form of a ready-mix or tank mix.

Suitable active compounds which can be combined with the active compounds according to the invention in mixed formulations or in a tank mix are, for example, known active compounds as described in for example *World Herbicide New Product Technology Handbook*, China Agricultural Science and Farming Techniques Press, 2010.9 and in the literature cited therein. For example the following active compounds may be mentioned as herbicides which can be combined with the compounds of the formula (I) (note: the compounds are either named by the "common name" in accordance with the International Organization for Standardization (ISO) or by the chemical names, if appropriate together with a customary code number): acetochlor, butachlor, alachlor, propisochlor, metolachlor, s-metolachlor, pretilachlor, propachlor, ethachlor, napropamide, R-left handed napropamide, propanil, mefenacet, diphenamid, diflufenican, ethaprochlor, beflubutamid, bromobutide, dimethenamid, dimethenamid-P, etobenzanid, flufenacet, thenylchlor, metazachlor, isoxaben, flamprop-M-methyl, flamprop-M-propyl, allidochlor, pethoxamid, chloranocryl, cyprazine, mefluidide, monalide, delachlor, prynachlor, terbuchlor, xylachlor, dimethachlor, cisanilide, trimexachlor, clomeprop, propyzamide, pentanochlor, carbetamide, benzoylprop-ethyl, cyprazole, butenachlor, tebutam, benzipram, 1379, dichlofluanid, naproanilide, diethatyl-ethyl, naptalam, flufenacet, benzadox, chlorthiamid, chlorophthalimide, isocarbamide, picolinafen, atrazine, simazine, prometryn, cyanatryn, simetryn, ametryn, propazine, dipropetryn, SSH-108, terbutryn, terbuthylazine, triaziflam, cyprazine, proglinazine, trietazine, prometon, simetone, aziprotryne, desmetryn, dimethametryn, procyazine, mesoprazine, sebuthylazine, secbumeton, terbumeton, methoprotryne, cyanatryn, ipazine, chlorazine, atraton, pendimethalin, eglinazine, cyanuric acid, indaziflam, chlorsulfuron, metsulfuron-methyl, bensulfuron methyl, chlorimuron-ethyl, tribenuron-methyl, thifensulfuron-methyl, pyrazosulfuron-ethyl, mesosulfuron, iodosulfuron-methyl sodium, foramsulfuron, cinosulfuron, triasulfuron, sulfometuron methyl, nicosulfuron, ethametsulfuron-methyl, amidosulfuron, ethoxysulfuron, cyclosulfamuron, rimsulfuron, azimsulfuron, flazasulfuron, monosulfuron, monosulfuron-ester, flucarbazone-sodium, flupyrsulfuron-methyl, halosulfuron-methyl, oxasulfuron, imazosulfuron, primisulfuron, propoxycarbazone, prosulfuron, sulfosulfuron, trifloxysulfuron, triflusulfuron-methyl, tritosulfuron, sodium metsulfuron methyl, flucetosulfuron, HNPC-C, orthosulfamuron, propyrisulfuron, metazosulfuron, acifluorfen, fomesafen, lactofen, fluoroglycofen, oxyfluorfen, chlornitrofen, aclonifen, ethoxyfen-ethyl, bifenox, nitrofluorfen, chlomethoxyfen, fluorodifen, fluoronitrofen, furyloxyfen, nitrofen, TOPE, DMNP, PPG1013, AKH-7088, halosafen, chlortoluron, isoproturon, linuron, diuron, dymron, fluometuron, benzthiazuron, methabenzthiazuron, cumyluron, ethidimuron, isouron, tebuthiuron, buturon, chlorbromuron, methyldymron, phenobenzuron, SK-85, metobromuron, metoxuron, afesin, monuron, siduron, fenuron, fluothiuron, neburon, chloroxuron, noruron, isonoruron, 3-cyclooctyl-1, thiazfluron, tebuthiuron, difenoxuron, parafluron, methylamine tribunil, karbutilate, trimeturon, dimefuron, monisouron, anisuron, methiuron, chloreturon, tetrafluron, phenmedipham, phenmedipham-ethyl, desmedipham, asulam, terbucarb, barban, propham, chlorpropham, rowmate, swep, chlorbufam, carboxazole, chlorprocarb, fenasulam, BCPC, CPPC, carbasulam, butylate, benthiocarb, vernolate, molinate, triallate, dimepiperate, esprocarb, pyributicarb, cycloate, avadex, EPTC, ethiolate, orbencarb, pebulate, prosulfocarb, tiocarbazil, CDEC, dimexano, isopolinate, methiobencarb, 2,4-D butyl ester, MCPA-Na, 2,4-D isooctyl ester, MCPA isooctyl ester, 2,4-D sodium salt, 2,4-D dimethyla mine salt, MCPA-thioethyl, MCPA, 2,4-D propionic acid, high 2,4-D propionic acid salt, 2,4-D butyric acid, MCPA propionic acid, MCPA propionic acid salt, MCPA butyric acid, 2,4,5-D, 2,4,5-D propionic acid, 2,4,5-D butyric acid, MCPA amine salt, dicamba, erbon, chlorfenac, saison, TBA, chloramben, methoxy-TBA, diclofop-methyl, fluazifop-butyl, fluazifop-p-butyl, haloxyfop-methyl, haloxyfop-P, quizalofop-ethyl, quizalofop-p-ethyl, fenoxaprop-ethy, fenoxaprop-p-ethyl, propaquizafop, cyhalofop-butyl, metamifop, clodinafop-propargyl, fenthiaprop-ethyl, chloroazifop-propynyl, poppenate-methyl, trifopsime, isoxapyrifop, paraquat, diquat, oryzalin, ethalfluralin, isopropalin, nitralin, profluralin, prodinamine, benfluralin, fluchloraline, dinitramina, dipropalin, chlornidine, methalpropalin, dinoprop, glyphosate, anilofos, glufosinate ammonium, amiprophos-methyl, sulphosate, piperophos, bialaphos-sodium, bensulide, butamifos, phocarb, 2,4-DEP, H-9201, zytron, imazapyr, imazethapyr, imazaquin, imazamox, imazamox ammonium salt, imazapic, imazamethabenz-methyl, fluroxypyr, fluroxypyr isooctyl ester, clopyralid, picloram, trichlopyr, dithiopyr, haloxydine, 3,5,6-trichloro-2-pyridinol, thiazopyr, fluridone, aminopyralid, diflufenzopyr, triclopyr-butotyl, Cliodinate, sethoxydim, clethodim, cycloxydim, alloxydim, clefoxydim, butroxydim, tralkoxydim, tepraloxydim, buthidazole, metribuzin, hexazinone, metamitron, ethiozin, ametridione, amibuzin, bromoxynil, bromoxynil octanoate, ioxynil octanoate, ioxynil, dichlobenil, diphenatrile, pyraclonil, chloroxynil, iodobonil, flumetsulam, florasulam, penoxsulam, metosulam, cloransulam-methyl, diclosulam, pyroxsulam, benfuresate, bispyribac-sodium, pyribenzoxim, pyriftalid, pyriminobac-methyl, pyrithiobac-sodium, benzobicylon, mesotrione, sulcotrione, tembotrione, tefuryltrione, bicyclopyrone, ketodpiradox, isoxaflutole, clomazone, fenoxasulfone, methiozolin, fluazolate, pyraflufen-ethyl, pyrazolynate, difenzoquat, pyrazoxyfen, benzofenap, nipyraclofen, pyrasulfotole, topramezone, pyroxasulfone, cafenstrole, flupoxam, aminotriazole, amicarbazone, azafenidin, carfentrazone-ethyl, sulfentrazone, bencarbazone, benzfendizone, butafenacil, bromacil, isocil, lenacil, terbacil, flupropacil, cinidon-ethyl, flumiclorac-pentyl, flumioxazin, propyzamide, MK-129, flumezin, pentachlorophenol, dinoseb, dinoterb, dinoterb acetate, dinosam, DNOC, chloronitrophene, medinoterb acetate, dinofenate, oxadiargyl, oxadiazon, pentoxazone, Flufenacet, fluthiacet-methyl, fentrazamide, flufenpyr-ethyl, pyrazon, brompyrazon, metflurazon, kusakira, dimidazon, oxapyrazon, norflurazon, pyridafol, quinclorac, quinmerac, bentazone, pyridate, oxaziclomefone, benazolin, clomazone, cinmethylin, ZJ0702, pyribambenz-propyl, indanofan, sodium chlorate, dalapon, trichloroacetic acid, monochloroacetic acid, hexachloroacetone, flupropanate, cyperquat, bromofenoxim, epronaz, methazole, flurtamone, benfuresate, ethofumesate, tioclorim, chlorthal, fluorochloridone, tavron, acrolein, bentranil, tridiphane, chlorfenpropmethyl, thidiarizonaimin, phenisopham, busoxinone, methoxyphenone, saflufenacil, clacyfos, chloropon, alorac, diethamquat, etnipromid, iprymidam, ipfencarbazone, thiencarbazone-methyl, pyrimisulfan, chlorflurazole, tripropindan, sulglycapin, prosulfalin, cambendichlor, aminocyclopyrachlor, rodethanil, benoxacor, fenclorim, flurazole, fenchlorazole-ethyl, cloquintocet-mexyl, oxabetrinil, MG/91, cyometrinil, DKA-24, mefenpyr-diethyl, furilazole, fluxofenim, isoxadifen-ethyl, dichlormid, halauxifen-methyl, DOW848, UBH-509, D489, LS 82-556, KPP-300, NC-324, NC-330, KH-218, DPX-N8189, SC-0744, DOWC0535, DK-8910, V-53482, PP-600, MBH-001, KIH-9201, ET-751, KIH-6127 and KIH-2023.

For use, the formulations which are present in commercially available form are, if appropriate, diluted in the customary manner, for example using water in the case of wettable powders, emulsifiable concentrates, dispersions and water-dispersible granules. Products in the form of dusts, granules for soil application or broadcasting and sprayable solutions are usually not further diluted with other inert substances prior to use. The application rate of the compounds of the formula (I) required varies with the external conditions, such as temperature, humidity, the nature of the herbicide used and the like. It can vary within wide limits, for example between 0.001 and 1.0 kg/ha or more of active substance, but it is preferably between 0.005 and 750 g/ha, in particular between 0.005 and 250 g/ha.

In view of economics, variety and biological activity of a compound, we preferably synthesized several compounds, part of which are chosen and listed in the following table. The structure and corresponding information of a certain compound are shown in Table 1. The compound listed in Table 1 is aimed for further explication of the present invention, and should not be taken as any limit to the present invention. The subject of the present invention should not be interpreted by those skilled in the art as being limited to the following compounds. The physical property data related to the present invention has not been calibrated.

TABLE 1

Compound structure and 1H NMR data

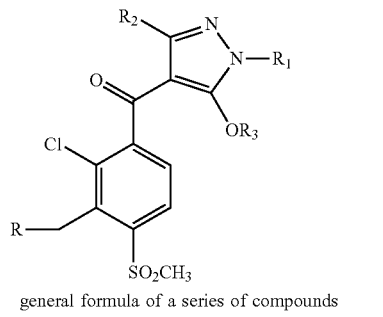

general formula of a series of compounds

| Serial NO. | $R_1$ | $R_2$ | $R_3$ | R | $^1$H NMR |
|---|---|---|---|---|---|
| 01 | —$CH_3$ | —$CH_3$ | —H | (4-methylpyrazol-1-yl) | $^1$H NMR (DMSO-$d_6$, 500 MHz): δ 1.99 (s, 3H), 2.12 (s, 3H), 3.26 (s, 3H), 3.37 (s, 3H), 3.91 (s, 1H), 5.95 (s, 2H), 7.45 (s, 1H), 7.62 (d, 1H, J = 8.0 Hz), 7.73 (s, 1H), 8.10 (d, 1H, J = 8.0 Hz). |
| 02 | —$CH_3$ | —$CH_3$ | —H | (pyrazol-1-yl) | $^1$H NMR (DMSO-$d_6$, 500 MHz): δ 2.08 (s, 3H), 3.28 (s, 3H), 3.35 (s, 3H), 3.90 (s, 1H), 5.97 (s, 2H), 6.26 (s, 1H), 7.44 (s, 1H), 7.60 (d, 1H, J = 8.0 Hz), 7.72 (s, 1H), 8.09 (d, 1H, J = 8.0 Hz). |
| 03 | —$CH_3$ | —$CH_3$ | —H | (3-methylpyrazol-1-yl) | $^1$H NMR (DMSO-$d_6$, 500 MHz): δ 2.05 (s, 3H), 2.16 (s, 3H), 3.29 (s, 3H), 3.41 (s, 3H), 3.91 (s, 1H), 5.99 (s, 2H), 6.32 (s, 1H), 7.58 (d, 1H, J = 8.0 Hz), 7.75 (s, 1H), 8.05 (d, 1H, J = 8.0 Hz). |
| 04 | —$CH_3$ | —$CH_3$ | —H | (3,5-dimethylpyrazol-1-yl) | $^1$H NMR (DMSO-$d_6$, 500 MHz): δ 2.02 (s, 3H), 2.10 (s, 3H), 2.15 (s, 3H), 3.30 (s, 3H), 3.45 (s, 3H), 3.91 (s, 1H), 5.92 (s, 2H), 6.38 (s, 1H), 7.61 (d, 1H, J = 8.0 Hz), 8.11 (d, 1H, J = 8.0 Hz). |
| 05 | —$CH_3$ | —$CH_2CH_3$ | —H | (4-chloropyrazol-1-yl) | $^1$H NMR (DMSO-$d_6$, 500 MHz): δ 1.20 (t, 3H, J = 7.0 Hz), 3.32 (s, 3H), 3.41 (s, 3H), 3.68 (q, 2H, J = 7.0 Hz), 3.91 (s, 1H), 5.93 (s, 2H), 7.39 (s, 1H), 7.56 (d, 1H, J = 8.0 Hz), 7.67 (s, 1H), 7.98 (d, 1H, J = 8.0 Hz). |
| 06 | —$CH_3$ | —$CH_2CH_3$ | —H | (pyrazol-1-yl) | $^1$H NMR (DMSO-$d_6$, 500 MHz): δ 1.15 (t, 3H, J = 7.0 Hz), 3.21 (s, 3H), 3.50 (s, 3H), 3.62 (q, 2H, J = 7.0 Hz), 3.89 (s, 1H), 5.85 (s, 2H), 6.23 (s, 1H), 7.31 (s, 1H), 7.51 (s, 1H), 7.71 (d, 1H, J = 8.0 Hz), 8.11 (d, 1H, J = 8.0 Hz). |
| 07 | —$CH_3$ | —H | —H | (4-methylpyrazol-1-yl) | $^1$H NMR (DMSO-$d_6$, 500 MHz): δ 1.99 (s, 3H), 3.27 (s, 3H), 3.52 (s, 3H), 3.90 (s, 1H), 5.89 (s, 2H), 7.23 (s, 1H), 7.33 (s, 1H), 7.49 (s, 1H), 7.69 (d, 1H, J = 8.0 Hz), 8.11 (d, 1H, J = 8.0 Hz). |

TABLE 1-continued

Compound structure and 1H NMR data (I)

*general formula of a series of compounds*

| Serial NO. | $R_1$ | $R_2$ | $R_3$ | R | $^1$H NMR |
|---|---|---|---|---|---|
| 08 | —CH$_3$ | —H | —H | 3-methyl-1-methyl-pyrazol-4-yl (CH$_3$ at 3-position) | $^1$H NMR (DMSO-d$_6$, 500 MHz): δ 2.21 (s, 3H), 3.37 (s, 3H), 3.59 (s, 3H), 3.92 (s, 1H), 5.96 (s, 2H), 6.28 (s, 1H), 7.37 (s, 1H), 7.54 (s, 1H), 7.66 (d, 1H, J = 8.0 Hz), 8.09 (d, 1H, J = 8.0 Hz). |
| 09 | —CH$_3$ | —H | —H | 3,5-dimethyl-1-methyl-pyrazol-4-yl | $^1$H NMR (DMSO-d$_6$, 500 MHz): δ 2.07 (s, 3H), 2.19 (s, 3H), 3.22 (s, 3H), 3.49 (s, 3H), 3.91 (s, 1H), 5.87 (s, 2H), 6.25 (s, 1H), 7.55 (s, 1H), 7.65 (d, 1H, J = 8.0 Hz), 7.99 (d, 1H, J = 8.0 Hz). |
| 10 | —CH$_3$ | —H | —H | 4-chloro-1-methyl-pyrazol-3-yl | $^1$H NMR (DMSO-d$_6$, 500 MHz): δ 3.16 (s, 3H), 3.43 (s, 3H), 3.92 (s, 1H), 5.91 (s, 2H), 7.21 (s, 1H), 7.30 (s, 1H), 7.53 (s, 1H), 7.66 (d, 1H, J = 8.0 Hz), 8.08 (d, 1H, J = 8.0 Hz). |
| 11 | —CH$_3$ | cyclopropyl | —H | 4-chloro-1-methyl-pyrazol-3-yl | $^1$H NMR (DMSO-d$_6$, 300 MHz): δ 0.67-1.42 (m, 4H), 2.39 (s, 1H), 3.14 (s, 3H), 3.77 (s, 3H), 3.90 (s, 1H), 5.81 (s, 2H), 7.55 (s, 1H), 7.64 (d, 1H, J = 7.8 Hz), 7.93 (d, 1H, J = 7.8 Hz), 8.06 (s, 1H). |
| 12 | —CH$_3$ | cyclopropyl | —H | 4-methyl-1-methyl-pyrazol-3-yl | $^1$H NMR (DMSO-d$_6$, 300 MHz): δ 0.61-1.38 (m, 4H), 1.95 (s, 3H), 2.41 (s, 1H), 3.16 (s, 3H), 3.55 (s, 3H), 3.90 (s, 1H), 5.84 (s, 2H), 7.57 (s, 1H), 7.62 (d, 1H, J = 7.8 Hz), 7.91 (d, 1H, J = 7.8 Hz), 8.07 (s, 1H). |
| 13 | —CH$_3$ | cyclopropyl | —H | 3,5-dimethyl-1-methyl-pyrazol-4-yl | $^1$H NMR (DMSO-d$_6$, 300 MHz): δ 0.64-1.40 (m, 4H), 2.23 (s, 3H), 2.39 (s, 1H), 3.14 (s, 3H), 3.53 (s, 3H), 3.77 (s, 3H), 3.90 (s, 1H), 5.81 (s, 2H), 6.28 (s, 1H), 7.64 (d, 1H, J = 7.8 Hz), 7.93 (d, 1H, J = 7.8 Hz). |
| 14 | —CH$_3$ | cyclopropyl | —H | 1-methyl-pyrazol-3-yl | $^1$H NMR (DMSO-d$_6$, 300 MHz): δ 0.70-1.47 (m, 4H), 2.23 (s, 3H), 2.39 (s, 1H), 3.53 (s, 3H), 3.90 (s, 1H), 5.98 (s, 2H), 6.26 (s, 1H), 7.43 (s, 1H), 7.65 (d, 1H, J = 7.8 Hz), 7.74 (s, 1H), 8.10 (d, 1H, J = 7.8 Hz). |

TABLE 1-continued

Compound structure and 1H NMR data

![General formula (I): pyrazole with R1, R2, OR3 substituents connected via carbonyl to chlorobenzene bearing CH2R and SO2CH3 groups]

general formula of a series of compounds

| Serial NO. | R₁ | R₂ | R₃ | R | ¹H NMR |
|---|---|---|---|---|---|
| 15 | —CH₂CH₃ | —CH₃ | —H | 1H-pyrazol-1-yl (N-methyl) | ¹H NMR (DMSO-d₆, 500 MHz): δ 1.18 (t, 3H, J = 7.0 Hz), 2.08 (s, 3H), 3.28 (s, 3H), 3.68 (q, 2H, J = 7.0 Hz), 3.90 (s, 1H), 5.97 (s, 2H), 6.26 (s, 1H), 7.44 (s, 1H), 7.60 (d, 1H, J = 8.0 Hz), 7.72 (s, 1H), 8.09 (d, 1H, J = 8.0 Hz). |
| 16 | —CH₂CH₃ | —CH₃ | —H | 4-methyl-1-methyl-1H-pyrazol-3-yl | ¹H NMR (DMSO-d₆, 500 MHz): δ 1.14 (t, 3H, J = 7.0 Hz), 1.99 (s, 3H), 2.12 (s, 3H), 3.26 (s, 3H), 3.65 (q, 2H, J = 7.0 Hz), 3.91 (s, 1H), 5.95 (s, 2H), 7.45 (s, 1H), 7.62 (d, 1H, J = 8.0 Hz), 7.73 (s, 1H), 8.10 (d, 1H, J = 8.0 Hz). |
| 17 | —CH₂CH₃ | —CH₃ | —H | 3,5-dimethyl-1-methyl-1H-pyrazol-4-yl | ¹H NMR (DMSO-d₆, 500 MHz): δ 1.16 (t, 3H, J = 7.0 Hz), 2.02 (s, 3H), 2.10 (s, 3H), 2.15 (s, 3H), 3.30 (s, 3H), 3.67 (q, 2H, J = 7.0 Hz), 3.91 (s, 1H), 5.92 (s, 2H), 6.38 (s, 1H), 7.61 (d, 1H, J = 8.0 Hz), 8.11 (d, 1H, J = 8.0 Hz). |
| 18 | —CH₂CH₃ | —H | —H | 1H-pyrazol-1-yl (N-methyl) | ¹H NMR (DMSO-d₆, 500 MHz): δ 1.15 (t, 3H, J = 7.0 Hz), 3.21 (s, 3H), 3.69 (q, 2H, J = 7.0 Hz), 3.89 (s, 1H), 5.85 (s, 2H), 6.23 (s, 1H), 7.20 (s, 1H), 7.31 (s, 1H), 7.51 (s, 1H), 7.71 (d, 1H, J = 8.0 Hz), 8.11 (d, 1H, J = 8.0 Hz). |
| 19 | —CH₂CH₃ | —H | —H | 4-methyl-1-methyl-1H-pyrazol-3-yl | ¹H NMR (DMSO-d₆, 500 MHz): δ 1.18 (t, 3H, J = 7.0 Hz), 1.99 (s, 3H), 3.27 (s, 3H), 3.66 (q, 2H, J = 7.0 Hz), 3.90 (s, 1H), 5.89 (s, 2H), 7.23 (s, 1H), 7.33 (s, 1H), 7.49 (s, 1H), 7.69 (d, 1H, J = 8.0 Hz), 8.10 (d, 1H, J = 8.0 Hz). |
| 20 | —CH₂CH₃ | —H | —H | 3,5-dimethyl-1-methyl-1H-pyrazol-4-yl | ¹H NMR (DMSO-d₆, 500 MHz): δ 1.17 (t, 3H, J = 7.0 Hz), 2.07 (s, 3H), 2.19 (s, 3H), 3.22 (s, 3H), 3.68 (q, 2H, J = 7.0 Hz), 3.91 (s, 1H), 5.87 (s, 2H), 6.25 (s, 1H), 7.55 (s, 1H), 7.65 (d, 1H, J = 8.0 Hz), 7.99 (d, 1H, J = 8.0 Hz). |

TABLE 1-continued

Compound structure and 1H NMR data

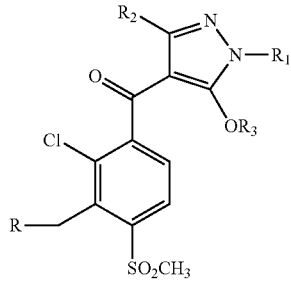

general formula of a series of compounds (I)

| Serial NO. | R₁ | R₂ | R₃ | R | ¹H NMR |
|---|---|---|---|---|---|
| 21 | —CH₂CH₃ | cyclopropyl | —H | pyrazol-1-yl | ¹H NMR (DMSO-d₆, 500 MHz): δ 0.70-1.47 (m, 7H), 2.22 (s, 3H), 2.38 (s, 1H), 3.67 (q, 2H, J = 7.0 Hz), 3.90 (s, 1H), 5.88 (s, 2H), 6.26 (s, 1H), 7.43 (s, 1H), 7.65 (d, 1H, J = 7.8 Hz), 7.74 (s, 1H), 8.10 (d, 1H, J = 7.8 Hz). |
| 22 | —CH₂CH₃ | cyclopropyl | —H | 4-methyl-pyrazol-1-yl | ¹H NMR (DMSO-d₆, 300 MHz): δ 0.61-1.38 (m, 7H), 1.95 (s, 3H), 2.41 (s, 1H), 3.16 (s, 3H), 3.69 (q, 2H, J = 7.0 Hz), 3.90 (s, 1H), 5.84 (s, 2H), 7.57 (s, 1H), 7.62 (d, 1H, J = 7.8 Hz), 7.91 (d, 1H, J = 7.8 Hz), 8.07 (s, 1H). |
| 23 | —CH₂CH₃ | cyclopropyl | —H | 3,5-dimethyl-pyrazol-1-yl | ¹H NMR (DMSO-d₆, 300 MHz): δ 0.64-1.40 (m, 7H), 2.23 (s, 3H), 2.39 (s, 1H), 3.14 (s, 3H), 3.65 (q, 2H, J = 7.0 Hz), 3.77 (s, 3H), 3.91 (s, 1H), 5.81 (s, 2H), 6.28 (s, 1H), 7.64 (d, 1H, J = 7.8 Hz), 7.93 (d, 1H, J = 7.8 Hz). |
| 24 | —CH₂CH₃ | —CH₂CH₃ | —H | pyrazol-1-yl | ¹H NMR (DMSO-d₆, 500 MHz): δ 1.08 (t, 3H, J = 7.0 Hz), 1.18 (t, 3H, J = 7.0 Hz), 2.74 (q, 2H, J = 7.0 Hz), 3.28 (s, 3H), 3.68 (q, 2H, J = 7.0 Hz), 3.90 (s, 1H), 5.97 (s, 2H), 6.26 (s, 1H), 7.44 (s, 1H), 7.60 (d, 1H, J = 8.0 Hz), 7.72 (s, 1H), 8.09 (d, 1H, J = 8.0 Hz). |
| 25 | —CH₂CH₃ | —CH₂CH₃ | —H | 4-methyl-pyrazol-1-yl | ¹H NMR (DMSO-d₆, 500 MHz): δ 1.05 (t, 3H, J = 7.0 Hz), 1.14 (t, 3H, J = 7.0 Hz), 1.99 (s, 3H), 2.72 (q, 2H, J = 7.0 Hz), 3.26 (s, 3H), 3.65 (q, 2H, J = 7.0 Hz), 3.91 (s, 1H), 5.95 (s, 2H), 7.45 (s, 1H), 7.62 (d, 1H, J = 8.0 Hz), 7.73 (s, 1H), 8.10 (d, 1H, J = 8.0 Hz). |
| 26 | —CH₂CH₃ | —CH₂CH₃ | —H | 3,5-dimethyl-pyrazol-1-yl | ¹H NMR (DMSO-d₆, 500 MHz): δ 0.99 (t, 3H, J = 7.0 Hz), 1.16 (t, 3H, J = 7.0 Hz), 2.10 (s, 3H), 2.15 (s, 3H), 2.77 (q, 2H, J = 7.0 Hz), 3.30 (s, 3H), 3.67 (q, 2H, J = 7.0 Hz), 3.91 (s, 1H), 5.92 (s, 2H), 6.38 (s, 1H), 7.61 (d, 1H, J = 8.0 Hz), 8.11 (d, 1H, J = 8.0 Hz). |

TABLE 1-continued

Compound structure and 1H NMR data

*general formula of a series of compounds (I)*

| Serial NO. | R₁ | R₂ | R₃ | R | ¹H NMR |
|---|---|---|---|---|---|
| 27 | -CH(CH₃)₂ | cyclopropyl | —H | 1H-pyrazol-1-ylmethyl | ¹H NMR (DMSO-d₆, 300 MHz): δ 0.70-1.47 (m, 10H), 2.22 (s, 3H), 2.38 (s, 1H), 3.62-3.72 (m, 1H), 3.90 (s, 1H), 5.88 (s, 2H), 6.26 (s, 1H), 7.43 (s, 1H), 7.65 (d, 1H, J = 7.8 Hz), 7.74 (s, 1H), 8.10 (d, 1H, J = 7.8 Hz). |
| 28 | -CH(CH₃)₂ | —H | —H | 4-methyl-1H-pyrazol-1-ylmethyl | ¹H NMR (DMSO-d₆, 500 MHz): δ 1.18 (d, 6H, J = 7.0 Hz), 1.99 (s, 3H), 3.27 (s, 3H), 3.66-3.77 (m, 1H), 3.90 (s, 1H), 5.89 (s, 2H), 7.23 (s, 1H), 7.33 (s, 1H), 7.49 (s, 1H), 7.69 (d, 1H, J = 8.0 Hz), 8.10 (d, 1H, J = 8.0 Hz). |
| 29 | -CH(CH₃)₂ | —CH₂CH₃ | —H | 3,5-dimethyl-1H-pyrazol-1-ylmethyl | ¹H NMR (DMSO-d₆, 500 MHz): δ 1.05-1.12 (m, 9H), 2.08 (s, 3H), 2.18 (s, 3H), 2.69 (q, 2H, J = 7.0 Hz), 3.41 (s, 3H), 3.60-3.71 (m, 1H), 3.90 (s, 1H), 5.90 (s, 2H), 6.42 (s, 1H), 7.66 (d, 1H, J = 8.0 Hz), 8.12 (d, 1H, J = 8.0 Hz). |
| 30 | -CH(CH₃)₂ | —CH₃ | —H | 4-chloro-1H-pyrazol-1-ylmethyl | ¹H NMR (DMSO-d₆, 500 MHz): δ 1.20 (d, 6H, J = 7.0 Hz), 2.32 (s, 3H), 3.41 (s, 3H), 3.65-3.74 (m, 1H), 3.91 (s, 1H), 5.93 (s, 2H), 7.39 (s, 1H), 7.56 (d, 1H, J = 8.0 Hz), 7.67 (s, 1H), 7.98 (d, 1H, J = 8.0 Hz). |
| 31 | —CH₃ | —CH₃ | -C(O)OCH₂CH₃ | 4-methyl-1H-pyrazol-1-ylmethyl | ¹H NMR (DMSO-d₆, 500 MHz): δ 1.14 (t, 3H, J = 7.0 Hz), 1.99 (s, 3H), 2.18 (s, 3H), 3.31 (s, 3H), 3.45 (s, 3H), 4.05 (q, 2H, J = 7.0 Hz), 5.98 (s, 2H), 7.44 (s, 1H), 7.65 (d, 1H, J = 8.0 Hz), 7.77 (s, 1H), 8.09 (d, 1H, J = 8.0 Hz). |
| 32 | —CH₃ | —CH₃ | -S(O)₂CH₂CH₃ | 4-methyl-1H-pyrazol-1-ylmethyl | ¹H NMR (DMSO-d₆, 500 MHz): δ 1.54 (t, 3H, J = 7.5 Hz), 1.98 (s, 3H), 2.13 (s, 3H), 3.30 (s, 3H), 3.42 (s, 3H), 3.55 (q, 2H, J = 7.5 Hz), 5.96 (s, 2H), 7.42 (s, 1H), 7.66 (d, 1H, J = 8.0 Hz), 7.78 (s, 1H), 8.10 (d, 1H, J = 8.0 Hz). |

TABLE 1-continued

Compound structure and 1H NMR data

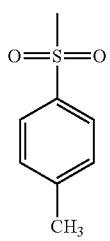

general formula of a series of compounds

| Serial NO. | $R_1$ | $R_2$ | $R_3$ | R | $^1$H NMR |
|---|---|---|---|---|---|
| 33 | —CH$_3$ | —CH$_3$ | 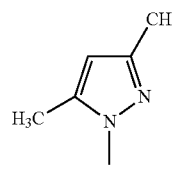 | 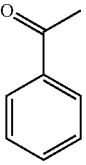 | $^1$H NMR (DMSO-d$_6$, 500 MHz): δ 1.66 (s, 3H), 1.96 (s, 3H), 2.29 (s, 3H), 2.35 (s, 3H), 3.21 (s, 3H), 3.66 (s, 3H), 5.70 (s, 2H), 5.84 (s, 1H), 6.81 (d, 2H, J = 8.0 Hz), 7.09 (d, 2H, J = 8.0 Hz), 7.72 (d, 1H, J = 8.0 Hz), 8.14 (d, 1H, J = 8.0 Hz). |
| 34 | —CH$_3$ | —CH$_3$ | 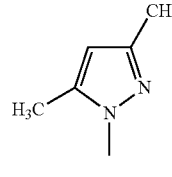 | 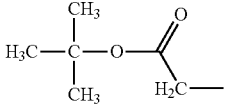 | $^1$H NMR (DMSO-d$_6$, 500 MHz): δ 1.62 (s, 3H), 1.93 (s, 3H), 2.38 (s, 3H), 3.23 (s, 3H), 3.64 (s, 3H), 5.76 (s, 2H), 5.88 (s, 1H), 6.93 (d, 2H, J = 8.0 Hz), 7.03 (t, 1H, J = 8.0 Hz), 7.30 (t, 2H, J = 8.0 Hz), 7.69 (d, 1H, J = 8.0 Hz), 8.11 (d, 1H, J = 8.0 Hz). |
| 35 | —CH$_3$ | —CH$_3$ | 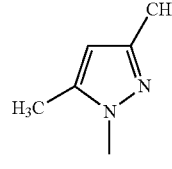 | 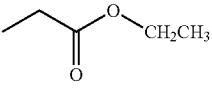 | $^1$H NMR (DMSO-d$_6$, 500 MHz): δ 1.40 (s, 9H), 1.65 (s, 3H), 1.95 (s, 3H), 2.34 (s, 3H), 3.20 (s, 3H), 3.65 (s, 3H), 4.90 (s, 2H), 5.71 (s, 2H), 5.83 (s, 1H), 7.70 (d, 1H, J = 8.0 Hz), 8.13 (d, 1H, J = 8.0 Hz). |
| 36 | —CH$_3$ | —CH$_3$ | 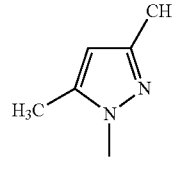 | 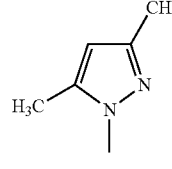 | $^1$H NMR (DMSO-d$_6$, 500 MHz): δ 1.26 (t, 3H, J = 7.0 Hz), 1.64 (s, 3H), 1.93 (s, 3H), 2.33 (s, 3H), 3.18 (s, 3H), 3.66 (s, 3H), 4.18 (q, 2H, J = 7.0 Hz), 5.70 (s, 2H), 5.82 (s, 1H), 7.72 (d, 1H, J = 8.0 Hz), 8.12 (d, 1H, J = 8.0 Hz). |
| 37 | —CH$_3$ | —CH$_3$ | —CH$_2$CH$_3$ | 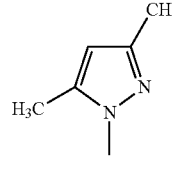 | $^1$H NMR (DMSO-d$_6$, 500 MHz): δ 0.96 (t, 3H, J = 7.0 Hz) 1.68 (s, 3H), 1.97 (s, 3H), 2.37 (s, 3H), 3.23 (s, 3H), 3.69 (s, 3H), 3.93 (q, 2H, J = 7.0 Hz), 5.74 (s, 2H), 5.85 (s, 1H), 7.69 (d, 1H, J = 8.0 Hz), 8.10 (d, 1H, J = 8.0 Hz). |
| 38 | —CH$_3$ | —CH$_3$ | —CH$_2$CH$_2$CH$_2$CH$_2$CH$_3$ | | $^1$H NMR (DMSO-d$_6$, 500 MHz): δ 0.90-1.15 (m, 9H), 1.66 (s, 3H), 1.99 (s, 3H), 2.39 (s, 3H), 3.25 (s, 3H), 3.71 (s, 3H), 3.82 (q, 2H, J = 7.0 Hz), 5.72 (s, 2H), 5.86 (s, 1H), 7.70 (d, 1H, J = 8.0 Hz), 8.10 (d, 1H, J = 8.0 Hz). |

TABLE 1-continued

Compound structure and 1H NMR data

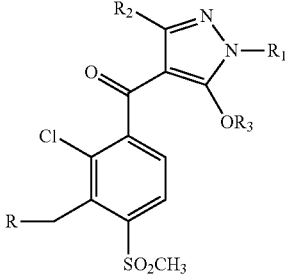

general formula of a series of compounds

| Serial NO. | $R_1$ | $R_2$ | $R_3$ | R | $^1$H NMR |
|---|---|---|---|---|---|
| 39 | —$CH_3$ | —$CH_3$ | 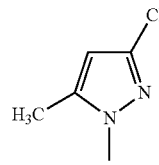 | 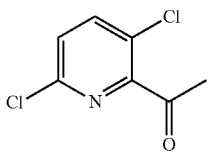 | $^1$H NMR (DMSO-$d_6$, 500 MHz): δ 1.64 (s, 3H), 1.93 (s, 3H), 2.06 (s, 3H), 2.33 (s, 3H), 3.18 (s, 3H), 3.66 (s, 3H), 5.70 (s, 2H), 5.82 (s, 1H), 7.72 (d, 1H, J = 8.0 Hz), 8.12 (d, 1H, J = 8.0 Hz). |
| 40 | —$CH_3$ | —$CH_3$ | 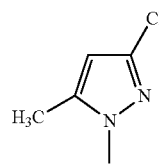 | 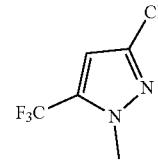 | $^1$H NMR (DMSO-$d_6$, 500 MHz): δ 1.66 (s, 3H), 1.93 (s, 3H), 2.34 (s, 3H), 3.22 (s, 3H), 3.68 (s, 3H), 5.71 (s, 2H), 5.86 (s, 1H), 7.46 (d, 1H, J = 8.0 Hz), 7.71 (d, 1H, J = 8.0 Hz), 7.78 (d, 1H, J = 8.0 Hz), 8.16 (d, 1H, J = 8.0 Hz). |
| 41 | —$CH_3$ | —$CH_3$ | —H | (see structure) | $^1$H NMR (DMSO-$d_6$, 500 MHz): δ 2.02 (s, 3H), 2.15 (s, 3H), 3.30 (s, 3H), 3.91 (s, 1H), 5.92 (s, 2H), 6.38 (s, 1H), 7.61 (d, 1H, J = 8.0 Hz), 8.11 (d, 1H, J = 8.0 Hz). |

SPECIFIC MODE FOR CARRYING OUT THE INVENTION

The above described content of the present invention is further explained through the following embodiments, and should not be interpreted by those skilled in the art as being limited to the embodiments: any techniques achieved on the basis of the content of the present invention should be included within the scope of the present invention. The technological parameters and production yield in the embodiments are presented without optimization.

Example 1

The method for preparing compound 01 in Table 1 is explicated in the embodiment

Step 1: The Synthesis of Intermediate (a)

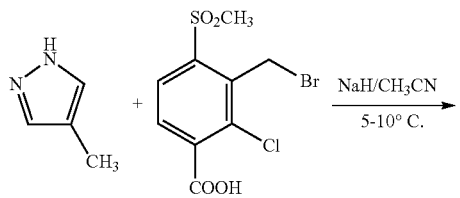

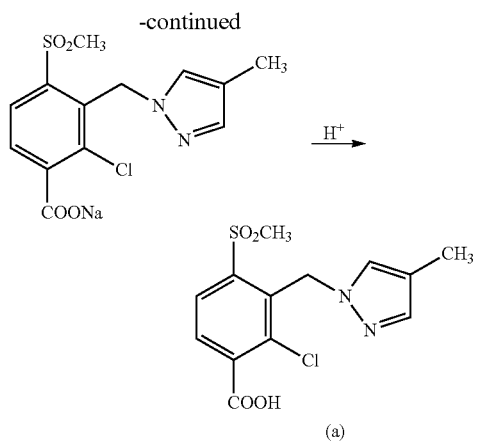

50 ml of acetonitrile was added into a 250 ml three-necked flask. The flask was placed in an ice-water bath, and the temperature was controlled at 5 to 10° C. 3.0 g (0.075 mol) of NaH was weighed and slowly added into the three-necked flask. The temperature was controlled below 10° C. Then 3 g (0.036 mol) of 4-methylpyrazole was dissolved into a little amount of acetonitrile, the solution was put into a dropping funnel and added dropwise to the system at about 0° C. The obtained mixture was stirred under the condition of ice-water bath after the addition. When the temperature of the system was stable, 10 g (0.030 mol) of 2-chloro-3-bromomethyl-4-methylsulfonylbenzoic acid was weighed and added slowly into the system in batches at a controlled temperature of no higher than 10° C. The system was stirred in the ice-water bath. The reaction was tracked by HPLC until the material was consumed completely. Acetonitrile was removed by rotary evaporation. 200 ml of water was added to the residue. HCl was added dropwise, the obtained mixture was stirred at room temperature to precipitate solid particles. The solid particles were collected by sucking filtration to obtain an off-white solid, which was intermediate (a). The intermediate was dried in a drying oven for further use.

Step 2: The Synthesis of Intermediate (b)

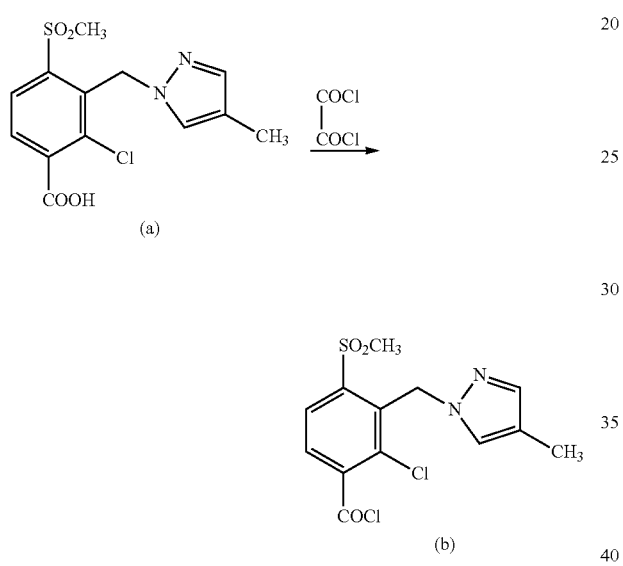

10 g (0.030 mol) of intermediate (a) was weighed and added into a 250 ml flask, then added with 50 ml of dichloroethane and a little amount of DMF as catalyst. Then 5 g (0.039 mol) of oxalyl chloride was dissolved into a little amount of dichloroethane. The solution was put into a dropping funnel, and dropped to the system at room temperature. The system was continued to agitate for about 2 hours at room temperature after the dropping to obtain the reaction solution containing intermediate (b). The reaction solution was directly used for the next reaction without any treatment.

Step 3: The Synthesis of Compound 01

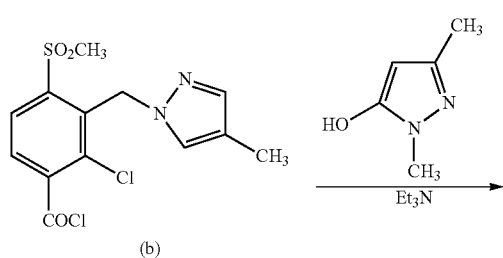

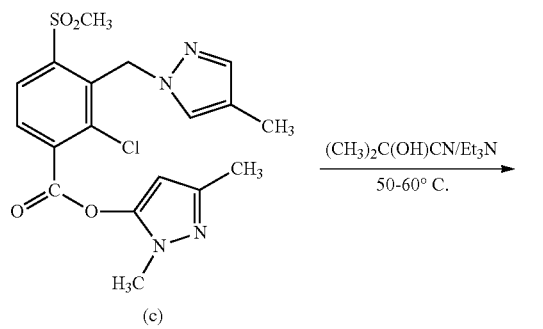

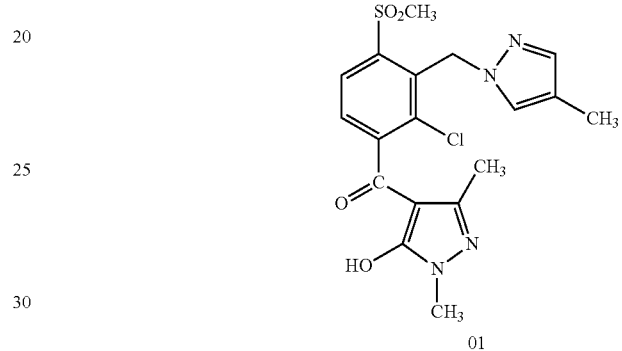

4.0 g (0.036 mol) of 1,3-dimethyl-5-pyrazol-ol was weighed and added into a 250 ml three-necked flask. 50 ml of 1,2-dichloroethane was added for dissolution. 12 g (0.12 mol) of triethylamine was weighed and added into the system. The reaction solution containing intermediate (b) (0.030 mol) was dropped into the system under the condition of ice-water bath and argon protection. The reaction was tracked with HPLC after 1 hour. The reaction solution containing intermediate (c) was obtained after the raw material was consumed completely. 3.0 g (0.030 mol) of triethylamine and 0.5 ml of acetone cyanohydrins were added into the reaction solution containing intermediate (c) with an argon protection, at a controlled temperature of 50 to 60° C., and reacted for 2 hours. HPLC was used to track the reaction. 100 ml water was added when the reaction was complete, then slowly dropped with HCl with stirring at room temperature until pH was adjusted to about 3. The aqueous layer was removed by extraction. The organic layer was washed for 2 times with 200 ml of water, dried with anhydrous sodium sulfate, the organic solvent was removed by rotary evaporation to obtain 8.1 g of pale brown powder solid, i.e. compound 01. The content determined by HPLC was 93.9% and the yield was 67.8%.

$^1$H NMR data see Table 1.

Examples 2-4 disclosed the synthesis of compound 02 to compound 04, respectively, the synthetic methods of which were similar to that of Example 1, hence their description was not given here.

Example 5

The example disclosed the synthesis of compound 05 in Table 1.

Step 1: The Synthesis of Intermediate (d)

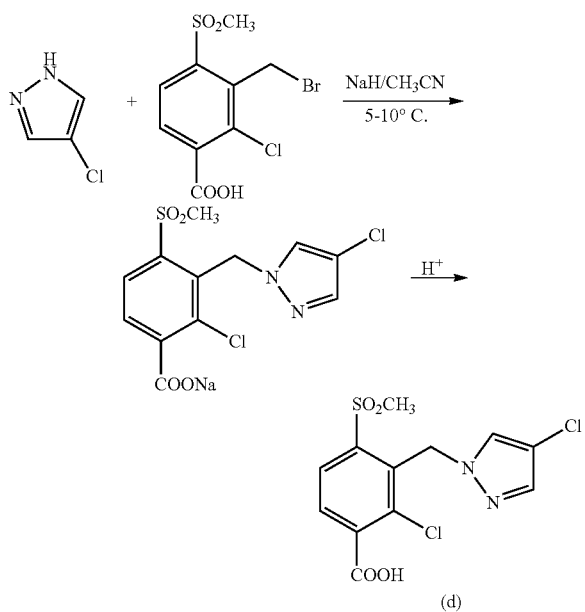

50 ml of acetonitrile was weighed and added into a 250 ml three-necked flask, and placed into an ice-water bath at a controlled temperature of 5 to 10° C. 4.4 g (0.11 mol) of NaH was weighed and slowly added into the flask at a controlled temperature of no higher than 10° C. 4.6 g (0.045 mol) of 4-chloropyrazole was weighed and dissolved with a little amount of acetonitrile, the solution was put into a dropping funnel and added dropwise when the system was cooled to about 0° C. The obtained reaction solution was kept stirring in the ice-water bath after the addition. After the temperature of the system was stable, 10 g (0.030 mol) of 2-chloro-3-bromomethyl-4-methylsulfonylbenzoic acid was weighed and added into the system in batches at a controlled temperature of no higher than 10° C. and kept stirring in the ice-water bath. The reaction was tracked with HPLC until the raw material was consumed completely. Acetonitrile was removed by rotary evaporation. 200 ml of water was added to the residue, then HCl was slowly added dropwise and stirred at room temperature to precipitate solid particles. The solid particles were collected by sucking filtration to obtain an off-white solid, i.e. intermediate (d). The intermediate was dried in a drying oven for further use.

Step 2: The Synthesis of Intermediate (e)

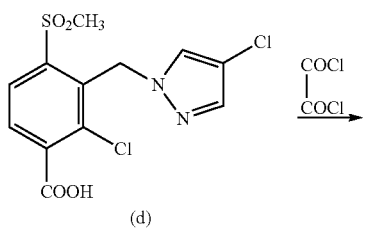 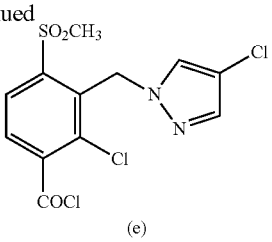

10.5 g (0.030 mol) of intermediate (d) was weighed and added into a 250 ml flask, and added with 50 ml of dichloroethane and a little amount of DMF as catalyst. Then 5 g (0.039 mol) of oxalyl chloride was weighed and dissolved into a little amount of dichloroethane. The solution was put into a dropping funnel and dropped into the system at room temperature. The system was kept stirring for about 2 hours at room temperature after the addition to obtain the reaction solution containing intermediate (e). The reaction solution was directly used for the next reaction without any treatment.

Step 3: Synthesis of Compound 05

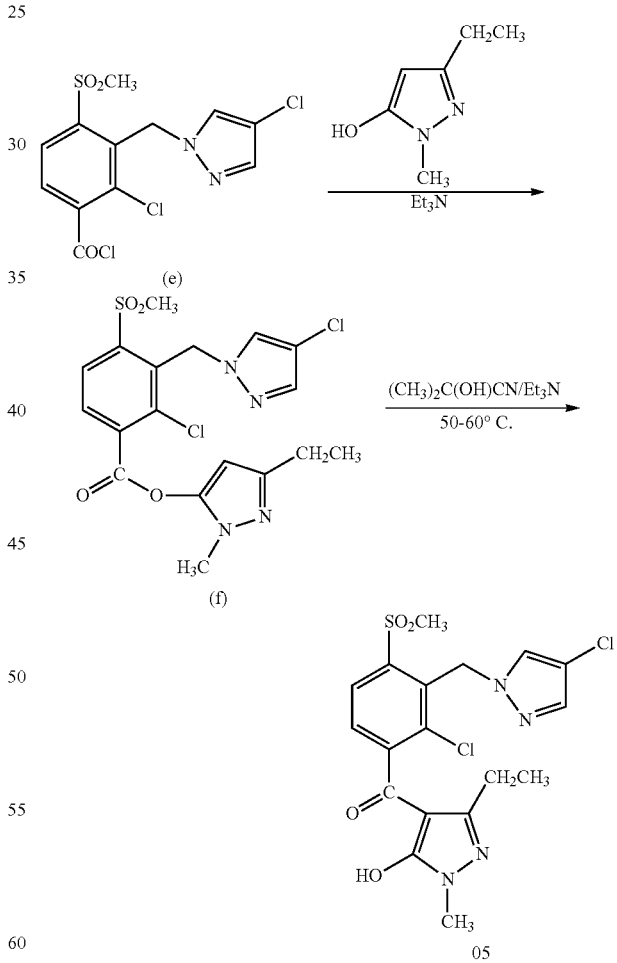

4.5 g (0.036 mol) of 1-methyl-3-ethyl-5-pyrazol-ol was weighed and added into a 250 ml three-necked flask, and added with 50 ml of 1,2-dichloroethane for dissolution. 12 g (0.012 mol) of triethylamine was weighed and put into the system. The reaction solution containing intermediate (e)

(0.030 mol) was dropped into the system in an ice-water bath with an argon protection. The reaction was tracked with HPLC after one hour, the reaction solution containing intermediate (f) was obtained after the raw material was consumed completely. 3.0 g (0.030 mol) of triethylamine and 0.5 ml of acetone cyanohydrin were added into the reaction solution containing intermediate (f) with an argon protection, at a controlled temperature of 40 to 50° C., and reacted for 2 hours. The reaction was tracked with HPLC. 100 ml of water was added after the reaction was complete, then HCl was slowly added dropwise with stirring at room temperature until pH was adjusted to about 3. The aqueous layer was removed by extraction, and the organic layer was washed for 2 times with 200 ml of water, dried with anhydrous sodium sulfate, the organic solvent was removed by rotary evaporation to obtain 6.7 g of dark brown powder solid, i.e. compound 05. The content determined by HPLC was 86.8% and the yield was 42.4%.

$^1$H NMR data see Table 1.

Example 6 disclosed the synthesis of compound 6, the synthetic method of which was similar to that of Example 5, hence its description was not given here Example 7

The example disclosed the synthesis of compound 07 in Table 1.

Step 1: The Synthesis of Intermediate (a)

See Example 1.

Step 2: The Synthesis of Intermediate (b)

See Example 1.

Step 3: The Synthesis of Compound 07

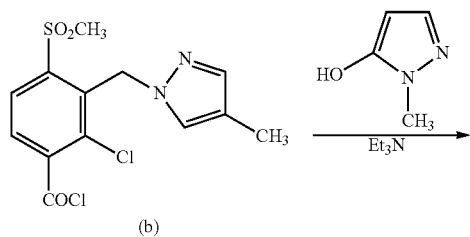

(b)

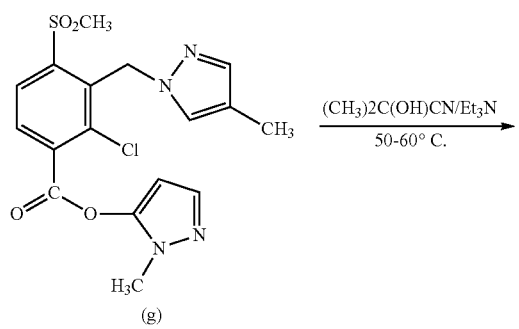

(g)

-continued

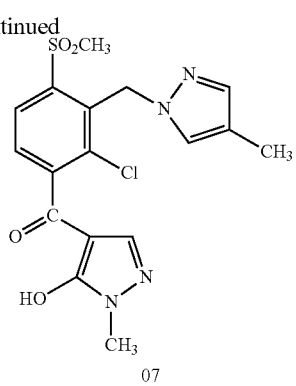

07

Weigh 3.2 g (0.033 mol) of 1-methyl-5-pyrazol-ol was weighed and added into a 250 ml three-necked flask, and added with 50 ml of 1,2-dichloroethane for dissolution. 10 g (0.010 mol) of triethylamine was added into the system. The reaction solution (0.030 mol) containing intermediate (b) was added dropwise under the condition of ice-water bath and argon protection. The reaction was tracked with HPLC after one hour of reacting, the reaction solution containing intermediate (g) was obtained after the raw material was consumed completely. 3.0 g (0.030 mol) of triethylamine and 0.5 ml of acetone cyanohydrin were added into the reaction solution containing intermediate (g) with argon protection at a controlled temperature of 50 to 60° C. The reaction was tracked with HPLC after 2 hours. 100 ml water was added when the reaction was complete, then slowly added dropwise with HCl with stirring at room temperature until pH was adjusted to about 3. The aqueous layer was removed by extraction. The organic layer was washed for 2 times with 200 ml water, dried with anhydrous sodium sulfate, concentrated by rotary evaporation to obtain 8.3 g of pale brown powder solid, i.e. compound 07. The content determined by HPLC was 96.5% and the yield was 72.4%.

$^1$H NMR data see Table 1.

Example 8 to Example 10 disclosed the synthesis of compound 08 to compound 10 in Table 1, respectively, the synthetic methods of which were similar to that of Example 7, hence their description was not given here.

Example 11

The example disclosed the synthesis of compound 11 in Table 1.

Step 1: Synthesis of Intermediate (d)

See Example 5.

Step 2: Synthesis of Intermediate (e)

See Example 5.

Step 3: Synthesis of Compound 11

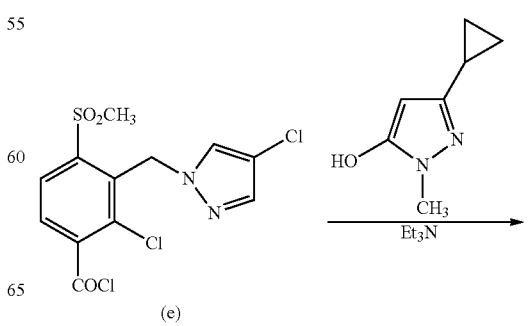

(e)

-continued

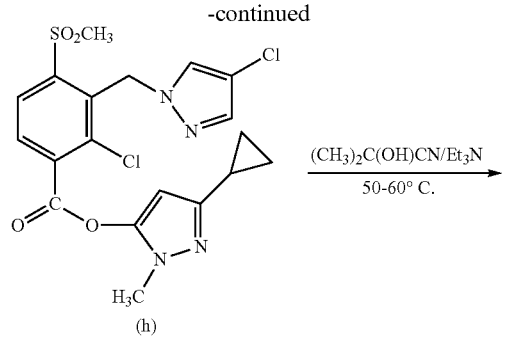

(h)

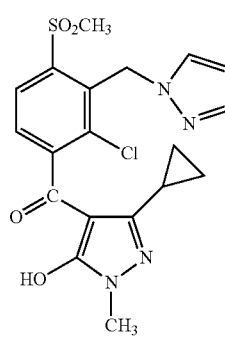

11

4.6 g (0.033 mol) of 1-methyl-3-cyclopropyl-5-pyrazol-ol was weighed and added into a 250 ml three-necked flask, and added with 50 ml of 1,2-dichloroethane for dissolution. 12 g (0.012 mol) of triethylamine was added into the system. The reaction solution containing intermediate (e) (0.030 mol) was dropped into the system under the condition of ice-water bath and argon protection. The reaction was tracked with HPLC after being reacted for 1 hour. The reaction solution containing intermediate (h) was obtained when the raw material were consumed completely. 3.0 g (0.030 mol) of triethylamine and 0.5 ml of acetone cyanohydrin were added into the reaction solution containing intermediate (h) with argon protection at a controlled temperature of 40 to 50° C. After reacting for 2 hours, the reaction was tracked with HPLC. 100 ml water was added when the reaction was complete, then slowly added with HCl drop by drop with stirring at room temperature until pH was adjusted to about 3. The aqueous layer was removed by extraction. The organic layer was washed for 2 times with 200 ml water, dried with anhydrous sodium sulfate, concentrated by rotary evaporation to obtain 6.6 g of dark brown powder solid, i.e. compound 11. The content determined by HPLC was 83.1% and the yield was 56.5%.

$^1$H NMR data see Table 1.

Example 12 to Example 14 disclosed the synthesis of compound 12 to compound 14 in Table 1, respectively, the synthetic methods of which were similar to that of Example 11, hence their description was not given here.

Example 15

The example disclosed the synthesis of compound 15 in Table 1.

Step 1: Synthesis of Intermediate (i)

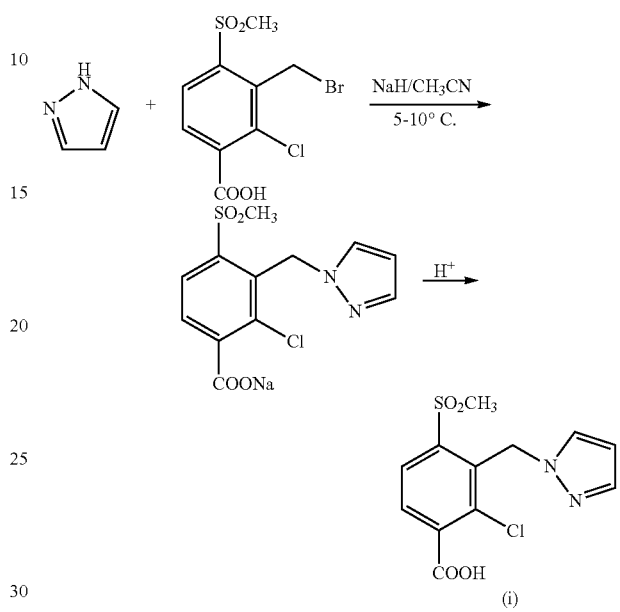

50 ml of acetonitrile was weighed and added into a 250 ml three-necked flask. The flask was placed in an ice-water bath for a controlled temperature of 5 to 10° C. 3.0 g (0.075 mol) of NaH was added into the flask slowly at a controlled temperature of 10° C. Then 2.4 g (0.036 mol) of pyrazole was dissolved into a little amount of acetonitrile, the obtained solution was put into a dropping funnel and added drop by drop when the temperature of the system was cooled to about 0° C. The system was kept stirring under the condition of ice-water bath after dropping. When the temperature of the system was stable, 10 g (0.030 mol) of 2-chloro-3-bromomethyl-4-methylsulfonyl benzoic acid was weighed and added slowly into the system in batches at a controlled temperature of no higher than 10° C. and stirred in the ice-water bath. The reaction was tracked with HPLC until the raw material was consumed completely. Acetonitrile was removed by rotary evaporation followed by an addition of 200 ml of water. HCl was added slowly drop by drop and stirred at room temperature to precipitate solid particles. The particle was collected by sucking filtration to obtain an off-white solid, i.e. intermediate (i). The intermediate was dried in a drying oven for further use.

Step 2: Synthesis of Intermediate (j)

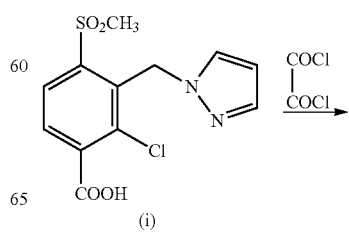

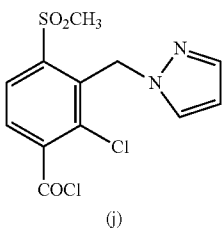
(j)

10 g (0.030 mol) of intermediate (i) was weighed and added into a 250 ml flask, and added with 50 ml of dichloroethane. A little amount of DMF was drop into as catalyst. Then 5 g (0.039 mol) of oxalyl chloride was weighed and dissolved into a little amount of dichloroethane, the obtained solution was put into a dropping funnel, and dropped to the system at room temperature. The system was stirred for about 2 hours at room temperature after the dropping to obtain the reaction solution containing intermediate (j). The reaction solution was directly used for the next reaction without any treatment.

Step 3: The Synthesis of Compound 15

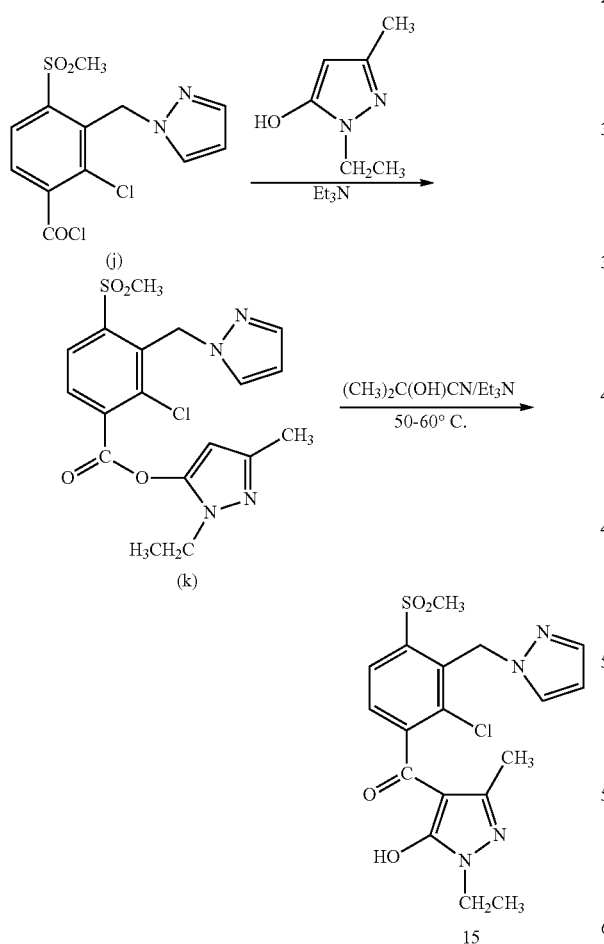

1.9 g (0.015 mol) of 1-methyl-3-cyclopropyl-5-pyrazol-ol was weighed and added into a 250 ml three-necked boiling flask, and added with 50 ml of 1,2-dichloroethane for dissolution. 4.0 g (0.040 mol) of triethylamine was weighed and added into the system. The 1,2-dichloroethane solution (containing 0.010 mol (j)) containing intermediate (j) was dropped into the system under the condition of ice-water bath and argon protection. The reaction was tracked with HPLC after reacting for 1 hour. The reaction solution containing intermediate (k) was obtained after the raw material was consumed completely. 1.0 g (0.010 mol) of triethylamine and several drops of acetone cyanohydrin was added into the reaction solution containing intermediate (k) under argon protection at a controlled temperature of 50 to 60° C., and reacted for 2 hours. The reaction was tracked with HPLC. 100 ml water was added when the reaction was complete, and added with HCl drop by drop slowly with stirring at room temperature until pH was adjusted to about 3. The aqueous layer was removed by extraction. The organic layer was washed for 2 times with 200 ml water, dried with anhydrous sodium sulfate, concentrated by rotary evaporation to obtain 3.6 g of pale brown powder solid, i.e. compound 15. The content determined by HPLC was 95.6% and the yield was 81.5%.

$^1$H NMR data see Table 1.

Example 16 to Example 17 disclosed the synthesis of compound 16 to compound 17 in Table 1, respectively, the synthetic methods of which were similar to that of Example 15, hence their description was not given here.

Example 18

The example disclosed the synthesis of compound 18 in Table 1.

Step 1: Synthesis of Intermediate (i)
See Example 15.
Step 2: Synthesis of Intermediate (j)
See Example 15.
Step 3: Synthesis of Compound 18

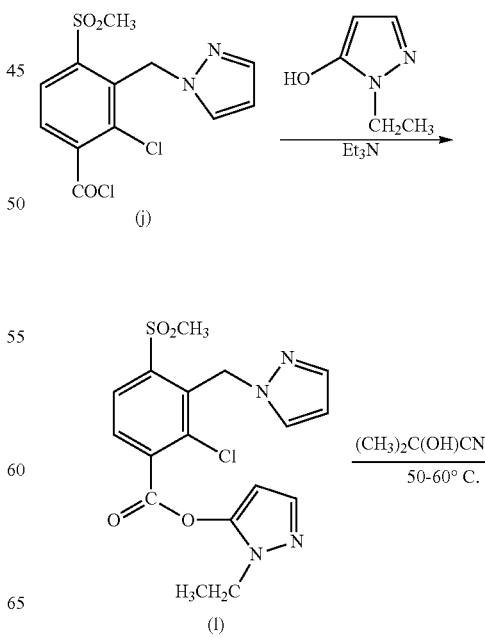

-continued

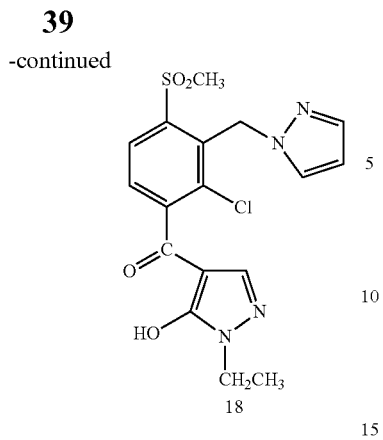

1.7 g (0.015 mol) of 1-ethyl-5-pyrazol-ol was weighed and added into a 250 ml three-necked flask, and added with 50 ml of 1,2-dichloroethane for dissolution. 4.0 g (0.040 mol) of triethylamine was weighed and added into the system. The 1,2-dichloroethane solution (containing 0.010 mol (j)) containing intermediate (j) was dropped into the system under the condition of ice-water bath and argon protection. The reaction was tracked with HPLC after reacting for 1 hour. The reaction solution containing intermediate (I) was obtained when the raw material was consumed completely. 1.0 g (0.010 mol) of triethylamine and several drops of acetone cyanohydrin were added into the reaction solution containing intermediate (I) at a controlled temperature of 50 to 60° C. under argon protection, and reacted for 2 hours. The reaction was tracked with HPLC. 100 ml water was added when the reaction was complete, then HCl was added drop by drop slowly with stirring at room temperature until pH was adjusted to about 3. The aqueous layer was removed by extraction. The organic layer was washed for 2 times with 200 ml water, dried with anhydrous sodium sulfate, concentrated by rotary evaporation to obtain 3.5 g of pale brown powder solid, i.e. compound 18. The content determined by HPLC was 94.9% and the yield was 81.3%.

$^1$H NMR data see Table 1.

Examples 19-20 disclosed the synthesis of compound 19 to compound 20 in Table 1, respectively, the synthetic methods of which were similar to that of Example 18, hence their description was not given here.

Example 21

The example disclosed the synthesis of compound 21 in Table 1.
Step 1: Synthesis of Intermediate (i)
See Example 15.
Step 2: Synthesis of Intermediate (j)
See Example 15.
Step 3: Synthesis of Compound 21

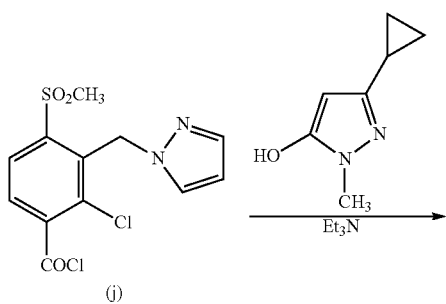

-continued

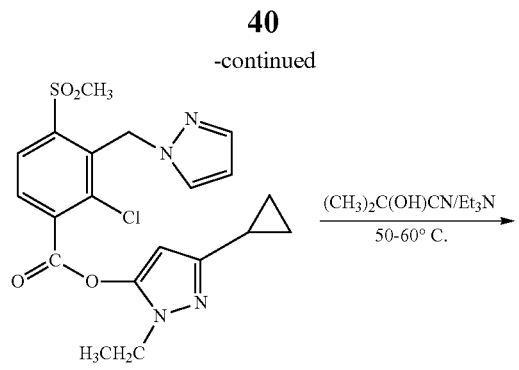

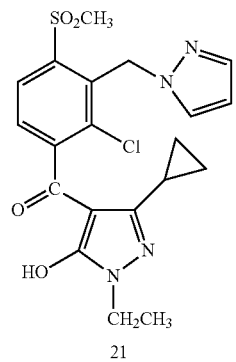

1.8 g (0.012 mol) of 1-methyl-3-cyclopropyl-5-pyrazol-ol was weighed and added into a 250 ml three-necked flask, and added with 50 ml of 1,2-dichloroethane for dissolution. 3.0 g (0.040 mol) of triethylamine was added into the system. The 1,2-dichloroethane solution (containing 0.010 mol (j)) containing intermediate (j) was dropped into the system under the condition of ice-water bath and argon protection. The reaction was tracked with HPLC after reacting for 1 hour. The reaction solution containing intermediate (m) was obtained when the material was consumed completely. 1.0 g (0.010 mol) of triethylamine and several drops of acetone cyanohydrin were added into the reaction solution containing intermediate (m) at a controlled temperature of 50 to 60° C. with argon protection, and reacted for 2 hours. The reaction was tracked with HPLC. 100 ml water was added when the reaction was complete, and HCl was added drop by drop slowly with stirring at room temperature until pH was adjusted to about 3. The aqueous layer was removed by extraction. The organic layer was washed for 2 times with 200 ml water, dried with anhydrous sodium sulfate, concentrated by rotary evaporation to obtain 3.9 g of pale brown powder solid, i.e. compound 21. The content determined by HPLC was 93.6% and the yield was 81.4%.

$^1$H NMR data see Table 1.

Example 22 to Example 23 disclosed the synthesis of compound 22 to compound 23 in Table 1, respectively, the synthetic methods of which were similar to that of Example 21, hence their description was not given here.

Example 24

The example disclosed the specific synthesis method for compound 24 in Table 1.
Step 1: Synthesis of Intermediate (i)
See Example 15.
Step 1: Synthesis of Intermediate (j)
See Example 15.
Step 3: Synthesis of Compound 24

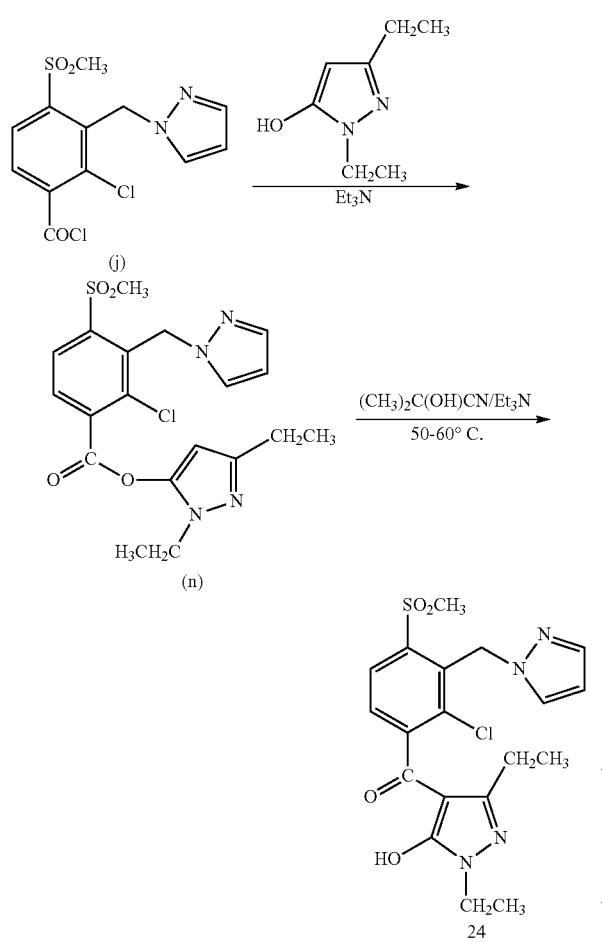

1.7 g (0.012 mol) of 1,3-diethyl-5-pyrazol-ol was weighed and added into a 250 ml three-necked flask, and 50 ml of 1,2-dichloroethane was added for dissolution. 3.0 g (0.030 mol) of triethylamine was weighed and added into the system. The 1,2-dichloroethane solution (containing 0.010 mol (j)) containing intermediate (j) was dropped into the system under the condition of ice-water bath and argon protection. The reaction was tracked with HPLC after reacting for 1 hour. The reaction solution containing intermediate (n) was obtained when the raw material was consumed completely. 1.0 g (0.010 mol) of triethylamine and several drops of acetone cyanohydrin were added into the reaction solution containing intermediate (n) at a controlled temperature of 50 to 60° C. under argon protection, and reacted for 2 hours. The reaction was tracked with HPLC. 100 ml water was added when the reaction was complete, followed by a slowly addition of HCl drop by drop with stirring at room temperature until pH was adjusted to about 3. The aqueous layer was removed by extraction. The organic layer was washed for 2 times with 200 ml water, dried with anhydrous sodium sulfate, concentrated by rotary evaporation to obtain 3.9 g of pale brown powder solid, i.e., compound 24. The content determined by HPLC was 92.1% and the yield was 82.3%.

$^1$H NMR data see Table 1.

Example 25 to Example 26 disclosed the synthesis of compound 25 to compound 26 in Table 1, respectively, the synthetic methods of which were similar to that of Example 24, hence their description was not given here.

Example 27

The example disclosed the synthesis of compound 24 in Table 1.
Step 1: Synthesis of Intermediate (i)
See Example 15.
Step 1: Synthesis of Intermediate (j)
See Example 15.
Step 3: Synthesis of Compound 27

The example disclosed the synthesis of compound 27 in Table 1. Compound 27 can be synthesized via the following route:

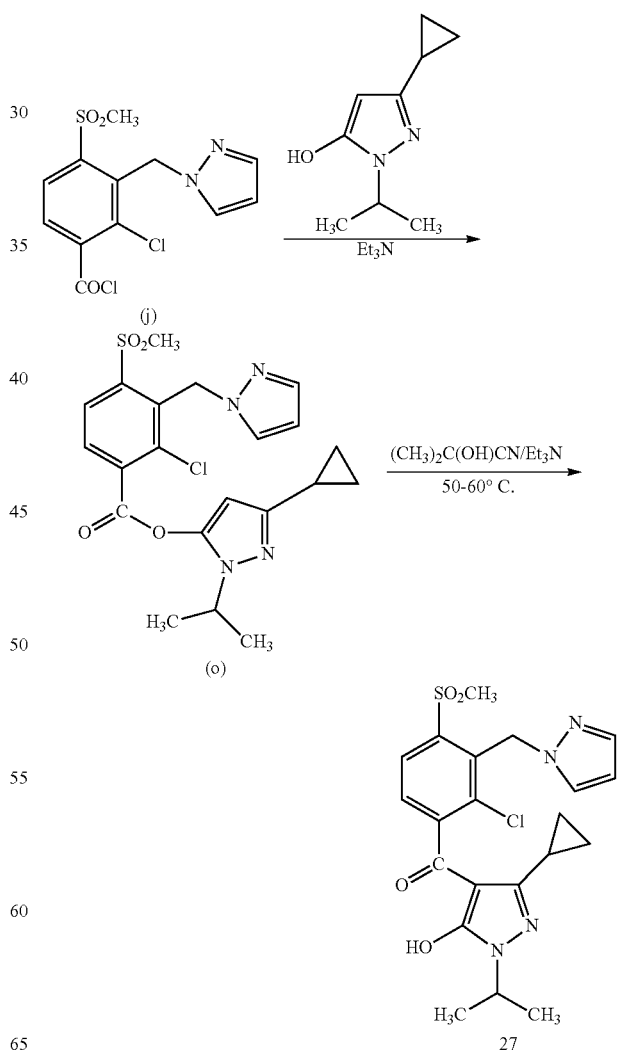

2.0 g (0.012 mol) of 1-isopropyl-3-cyclopropyl-5-pyrazol-ol was weighed and added into a 250 ml three-necked flask, and added with 50 ml of 1,2-dichloroethane for dissolution. 3.0 g (0.030 mol) of triethylamine was weighed and added into the system. The 1,2-dichloroethane solution (containing 0.010 mol (j)) containing intermediate (j) was added into the system under the condition of ice-water bath and argon protection. The reaction was tracked with HPLC after reacting for 1 hour. The reaction solution containing intermediate (o) was obtained when the raw material was consumed completely. 1.0 g (0.010 mol) of triethylamine and several drops of acetone cyanohydrin were added into the reaction solution containing intermediate (o) at a controlled temperature of 50 to 60° C. under argon protection, and reacted for 2 hours. The reaction was tracked with HPLC. 100 ml water was added when the reaction was complete followed by a slowly addition of HCl drop by drop slowly with stirring at room temperature until pH was adjusted to about 3. The aqueous layer was removed by extraction. The organic layer was washed for 2 times with 200 ml water, dried with anhydrous sodium sulfate, concentrated by rotary evaporation to obtain 4.0 g of pale brown powder solid, i.e. compound 27. The content determined by HPLC was 91.8% and the yield was 79.3%.

$^1$H NMR data see Table 1.

Example 28 to Example 30 disclosed the synthesis of compound 28 to compound 30 in Table 1, respectively, the synthetic methods of which were similar to that of Example 27, hence their description was not given here.

Example 31

The example disclosed the synthesis of compound 31 in Table 1. Compound 31 can be synthesized via the following route:

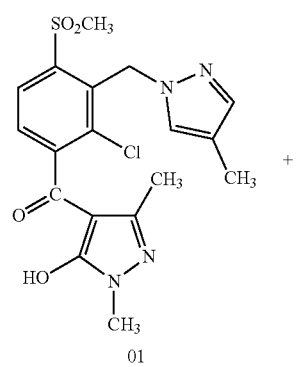

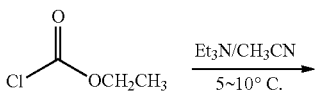

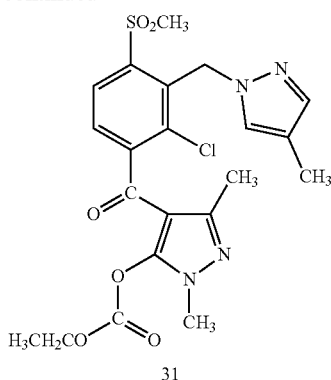

2.2 g (0.005 mol) of compound 01 was weighed and added into a 100 ml flask, 15 ml of acetonitrile and 1.0 g (0.010 mol) of triethylamine were added and stirred under the condition of ice-water bath. 0.9 g (0.007 mol) ethyl chloroformate was dissolved into 10 ml of acetonitrile and put into a dropping funnel, and dropped under the condition of ice-water bath. The mixture was reacted under homoeothermic condition in an ice-water bath after the dropping. The reaction was tracked with HPLC until compound 01 was consumed completely. 100 ml of water and 100 ml of ethyl acetate were added when the reaction was complete. The aqueous layer was removed by extraction. The organic layer was washed for 2 times with 100 ml of saturated salt solution, dried with anhydrous sodium sulfate, concentrated by rotary evaporation to obtain a pale brown powder solid. 1.4 g faint yellow powder, i.e. compound 31, was obtained after being recrystallized in 95% ethyl alcohol. The content determined by HPLC was 92.9% and the yield was 61.8%.

$^1$H NMR data see Table 1.

Example 32

The example disclosed the synthesis of compound 32 in Table 1. The compound 32 was synthesized via the following route:

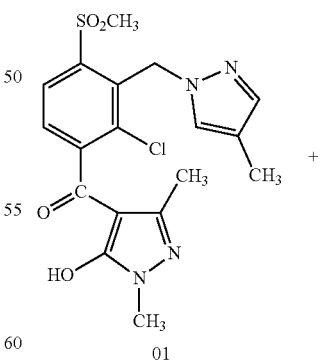

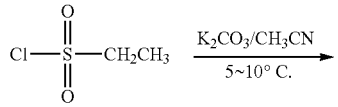

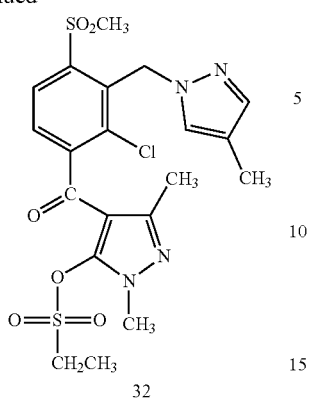

32

2.2 g (0.005 mol) of compound 01 was weighed and added into a 100 ml flask, 15 ml of acetonitrile and 1.4 g (0.010 mol) of potassium carbonate were added, and stirred under the condition of ice-water bath. 0.8 g (0.006 mol) ethanesulfonyl chloride was dissolved into 10 ml of acetonitrile and put into a dropping funnel, and dropped under the condition of ice-water bath. The mixture was reacted under homoeothermic condition in an ice-water bath after the dropping. The reaction was tracked with HPLC until compound 01 was consumed completely. 100 ml of water and 100 ml of ethyl acetate were added when the reaction was complete. The aqueous layer was removed by extraction. The organic layer was washed for 2 times with 100 ml of saturated salt solution, dried with anhydrous sodium sulfate, concentrated by rotary evaporation to obtain a yellow powder solid. 1.6 g faint yellow powder, i.e. compound 32, was obtained after being recrystallized in 95% ethyl alcohol. The content determined by HPLC was 95.1% and the yield was 65.3%.

$^1$H NMR data see Table 1.

Example 33

The example disclosed the synthesis of compound 33 in Table 1. The compound 33 was synthesized via the following route:

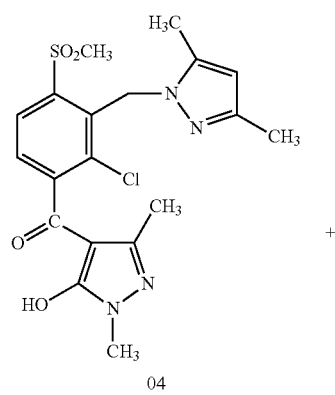

04

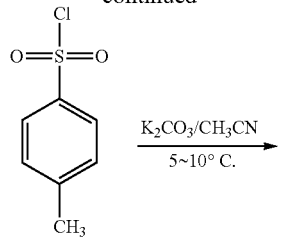

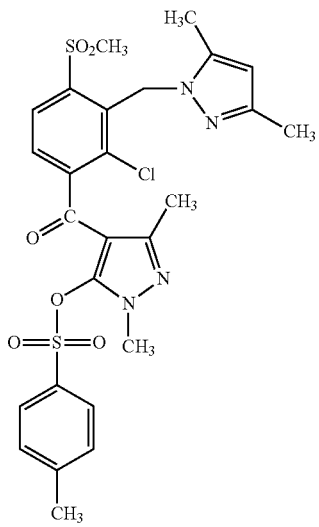

33

2.20 g (0.005 mol) of compound 04 was weighed and added into a 100 ml flask, 20 ml of acetonitrile and 1.40 g (0.010 mol) of potassium carbonate were added and stirred under the condition of ice-water bath. 0.95 g (0.005 mol) toluenesulfonyl chloride was dissolved into 10 ml of acetonitrile and put into a dropping funnel, and dropped under the condition of ice-water bath. The mixture was reacted under homoeothermic condition in an ice-water bath after the dropping. The reaction was tracked with HPLC until compound 04 was consumed completely. 100 ml of water and 100 ml of ethyl acetate were added when the reaction was complete. The aqueous layer was removed by extraction. The organic layer was washed for 2 times with 100 ml of saturated salt solution, dried with anhydrous sodium sulfate, concentrated by rotary evaporation to obtain a brown powder solid. 1.5 g light brown powder, i.e. compound 29, was obtained after being recrystallized in 95% ethyl alcohol. The content determined by HPLC was 95.5% and the yield was 48.5%.

$^1$H NMR data see Table 1.

Examples 34-40 disclosed the synthesis of compound 34 to compound 40 in Table 1, respectively, the synthetic methods of which were similar to that of Example 33, hence their description was not given here.

Biological Activity Evaluation:

The activity level standard of harmful plant damage (i.e. growth inhibition rate) is as follows:
Level 10: completely dead;
Level 9: above 90% growth inhibition rate;
Level 8: above 80% growth inhibition rate;
Level 7: above 70% growth inhibition rate;
Level 6: above 60% growth inhibition rate;
Level 5: above 50% growth inhibition rate;
Level 4: above 30% growth inhibition rate;

Level 3: above 30% growth inhibition rate;
Level 2: above 20% growth inhibition rate;
Level 1: above 1-10% growth inhibition rate;
Level 0: no effect The above described growth control rate is fresh weight control rate.

Monocotyledonous and dicotyledonous weed seeds and main crop seeds (i.e. wheat, corn, rice, soybean, cotton, oilseed, millet and *Sorghum*) were put into a plastic pot loaded with soil. Then covered with 0.5-2 cm soil, the seeds were allowed to grow in good greenhouse environment. The test plants were treated at 2-3 leaf stage 2-3 weeks after sowing. The test compounds of the invention were dissolved with acetone respectively, then added with 80 tween and diluted by certain amount of water to certain concentration. The solution was sprayed to the plants with a sprayer. Then the plants were cultured for 3 weeks in the greenhouse. The experiment result of weed controlling effect after 3 weeks was listed in table 2.

Table 2 indicates that many compounds of the present invention applied after emergence are safe to rice and have good efficacy on barnyard grass. At the same time, most compounds are also safe to corn and wheat and can be used in corn and wheat to control grass and broadleaf weeds.

Transplanted rice safety evaluation and weed control effect evaluation in rice field:

Rice field soil was loaded into a 1/1,000,000 ha pot. The seeds of *Echinochloa, Scirpus juncoides, Bidens tripartite* and *Sagittaria trifolia* were sowed and gently covered with soil, then left to stand still in greenhouse in the state of 0.5-1 cm of water storage. The tuber of *Sagittaria trifolia* was planted in the next day or 2 days later. It was kept at 3-4 cm of water storage thereafter. The weeds were treated by dripping the WP or SC water diluents prepared according to the common preparation method of the compounds of the present invention with pipette homogeneously to achieve specified effective amount when *Echinochloa, Scirpus juncoides* and

TABLE 2 experiment on weed control effect in post emergence stage

| Compound serial No. | Barnyard grass | | | | | Ning Jing 43 | | | | | Corn | Wheat | Flixweed |
|---|---|---|---|---|---|---|---|---|---|---|---|---|---|
| | 1 g/mu | 2 g/mu | 4 g/mu | 8 g/mu | 16 g/mu | 1 g/mu | 2 g/mu | 4 g/mu | 8 g/mu | 16 g/mu | 16 g/mu | 16 g/mu | 16 g/mu |
| 1 | 4 | 7 | 8 | 10 | 10 | 0 | 0 | 0 | 1 | 2 | 0 | 0 | 10 |
| 2 | 6 | 8 | 10 | 10 | 10 | 0 | 0 | 1 | 2 | 6 | 1 | 1 | 10 |
| 3 | 4 | 6 | 8 | 8 | 9 | 0 | 0 | 0 | 0 | 1 | 0 | 0 | 10 |
| 4 | 3 | 4 | 5 | 5 | 7 | 0 | 0 | 1 | 1 | 1 | 0 | 0 | 10 |
| 5 | 2 | 2 | 4 | 7 | 8 | 0 | 0 | 1 | 1 | 1 | 0 | 0 | 10 |
| 6 | 6 | 8 | 9 | 10 | 10 | 0 | 0 | 1 | 2 | 5 | 0 | 0 | 10 |
| 7 | 2 | 3 | 3 | 6 | 6 | 0 | 0 | 0 | 0 | 0 | 0 | 0 | 10 |
| 8 | 2 | 2 | 4 | 7 | 8 | 0 | 0 | 0 | 0 | 0 | 0 | 0 | 10 |
| 9 | 2 | 2 | 3 | 5 | 5 | 0 | 0 | 0 | 0 | 0 | 0 | 0 | 10 |
| 10 | 2 | 4 | 4 | 7 | 8 | 0 | 0 | 0 | 0 | 1 | 0 | 0 | 10 |
| 11 | 2 | 4 | 4 | 6 | 7 | 0 | 0 | 0 | 0 | 0 | 0 | 0 | 10 |
| 12 | 2 | 4 | 6 | 7 | 8 | 0 | 0 | 0 | 0 | 0 | 0 | 0 | 10 |
| 13 | 2 | 2 | 2 | 5 | 7 | 0 | 0 | 0 | 0 | 0 | 0 | 0 | 10 |
| 14 | 8 | 9 | 10 | 10 | 10 | 0 | 0 | 1 | 2 | 5 | 1 | 2 | 10 |
| 15 | 6 | 7 | 9 | 10 | 10 | 0 | 0 | 1 | 1 | 4 | 1 | 1 | 10 |
| 16 | 2 | 3 | 4 | 4 | 6 | 0 | 0 | 0 | 0 | 0 | 0 | 0 | 10 |
| 17 | 2 | 2 | 2 | 4 | 5 | 0 | 0 | 0 | 0 | 0 | 0 | 0 | 10 |
| 18 | 8 | 8 | 10 | 10 | 10 | 0 | 0 | 2 | 2 | 4 | 0 | 0 | 10 |
| 19 | 2 | 3 | 3 | 4 | 4 | 0 | 0 | 0 | 0 | 0 | 0 | 0 | 10 |
| 20 | 3 | 4 | 6 | 6 | 8 | 0 | 0 | 0 | 0 | 0 | 0 | 0 | 10 |
| 21 | 6 | 7 | 9 | 10 | 10 | 0 | 0 | 2 | 3 | 4 | 0 | 0 | 10 |
| 22 | 2 | 4 | 6 | 6 | 10 | 0 | 0 | 0 | 0 | 0 | 0 | 0 | 10 |
| 23 | 2 | 3 | 5 | 7 | 8 | 0 | 0 | 0 | 0 | 0 | 0 | 0 | 10 |
| 24 | 2 | 2 | 3 | 5 | 5 | 0 | 0 | 2 | 2 | 4 | 0 | 0 | 10 |
| 25 | 2 | 3 | 4 | 4 | 5 | 0 | 0 | 0 | 0 | 0 | 0 | 0 | 10 |
| 26 | 2 | 2 | 4 | 3 | 5 | 0 | 0 | 0 | 0 | 0 | 0 | 0 | 10 |
| 27 | 7 | 7 | 9 | 10 | 10 | 0 | 0 | 1 | 2 | 3 | 0 | 0 | 10 |
| 28 | 2 | 5 | 6 | 6 | 10 | 0 | 0 | 0 | 0 | 0 | 0 | 0 | 10 |
| 29 | 2 | 3 | 5 | 7 | 8 | 0 | 0 | 0 | 0 | 0 | 0 | 0 | 10 |
| 30 | 2 | 3 | 5 | 7 | 7 | 0 | 0 | 0 | 0 | 0 | 0 | 0 | 10 |
| 31 | 3 | 5 | 6 | 8 | 9 | 0 | 0 | 0 | 0 | 0 | 0 | 0 | 10 |
| 32 | 5 | 6 | 5 | 7 | 8 | 0 | 0 | 0 | 0 | 0 | 0 | 0 | 10 |
| 33 | 4 | 6 | 5 | 7 | 8 | 0 | 0 | 0 | 0 | 0 | 0 | 0 | 10 |
| 34 | 4 | 5 | 5 | 7 | 8 | 0 | 0 | 0 | 0 | 0 | 0 | 0 | 10 |
| 35 | 3 | 3 | 4 | 4 | 5 | 0 | 0 | 0 | 0 | 0 | 0 | 0 | 10 |
| 36 | 2 | 3 | 4 | 4 | 5 | 0 | 0 | 0 | 0 | 0 | 0 | 0 | 10 |
| 37 | 0 | 1 | 1 | 2 | 2 | 0 | 0 | 0 | 0 | 0 | 0 | 0 | 2 |
| 38 | 0 | 1 | 1 | 2 | 2 | 0 | 0 | 0 | 0 | 0 | 0 | 0 | 2 |
| 39 | 4 | 6 | 5 | 7 | 8 | 0 | 0 | 0 | 0 | 0 | 0 | 0 | 10 |
| 40 | 3 | 5 | 5 | 7 | 8 | 0 | 0 | 0 | 0 | 0 | 0 | 0 | 10 |
| 41 | 4 | 5 | 6 | 7 | 7 | 0 | 0 | 1 | 1 | 1 | 0 | 0 | 10 |

*Bidens tripartite* reached 0.5 leaf stage and *Sagittaria trifolia* reached the time point of primary leaf stage.

In addition, the rice field soil that loaded into the 1/1,000,000 ha pot was leveled to keep water storage at 3-4 cm depth. The 3 leaf stage rice (*japonica* rice) was transplanted at 3 cm of transplanting depth the next day. The compound of the present invention was treated by the same way after 5 days of transplantation.

The fertility condition of *Echinochloa, Scirpus juncoides, Bidens tripartite* and *Sagittaria trifolia* 14 days after the treatment of the compound of the invention and the fertility condition of rice 21 days after the treatment of the compound of the invention respectively with the naked eye. Evaluate the weed control effect with 1-10 activity standard level, which was presented in table 3.

TABLE 3 the experiment results of weed control effect in transplanted rice field (500 g a.i./ha)

| Compound serial No. | Barnyard grass | rushlike bulrush | Beggartick | Arrowhead | Rice |
|---|---|---|---|---|---|
| 1 | 10 | 10 | 9 | 8 | 0 |
| 2 | 10 | 10 | 10 | 10 | 3 |
| 3 | 10 | 10 | 10 | 8 | 0 |
| 4 | 10 | 10 | 9 | 9 | 0 |
| 5 | 10 | 10 | 10 | 10 | 1 |
| 13 | 10 | 9 | 9 | 9 | 0 |
| 15 | 10 | 9 | 9 | 8 | 2 |
| 18 | 10 | 9 | 10 | 10 | 1 |
| 28 | 10 | 10 | 10 | 8 | 0 |
| 31 | 10 | 10 | 10 | 9 | 1 |
| 33 | 10 | 10 | 10 | 10 | 1 |
| 35 | 10 | 10 | 10 | 9 | 0 |
| 39 | 10 | 10 | 8 | 6 | 0 |

Note: The seeds of barnyard grass, rushlike bulrush, arrowhead and beggartick are collected from Heilongjing Province of China. Tests indicate that the weeds are resistant to common application rate of pyrazosulfuron-ethyl.

At the same time, it is found after several tests that the compound of the present invention has good selectivity to many gramineae grass such as *Zoysia japonica*, bermuda grass, tall fescue, bluegrass, ryegrass and seashore paspalum etc, and is able to control many important grass weeds and broadleaf weeds. The compound also shows excellent selectivity and commercial value in the tests on soybean, cotton, oil sunflower, potato, orchards and vegetables in different herbicide application methods.

What is claimed is:

1. A pyrazole compound of formula (I) or a salt thereof:

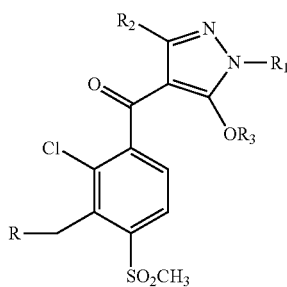

wherein,

R represents

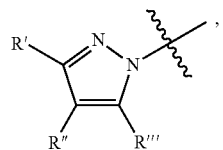

wherein, R', R", and R'" represent hydrogen, C1-C4 alkyl, C1-C4 halogenated alkyl, or halogen, wherein R', R", and R'" are the same or different, $R_1$ represents C1-C3 alkyl;

$R_2$ represents hydrogen or C1-C4 alkyl; and $R_3$ represents hydrogen, C1-C6 alkyl carbonyl, C1-C6 alkoxyl carbonyl, C1-C6 alkoxyl carbonyl methyl, C1-C4 alkyl sulfonyl, phenylsulfonyl substituted by alkyl, or benzoyl.

2. A method for preparing the pyrazole compound or the salt thereof according to claim 1 comprising the following steps:

(1) 2-chloro-3-bromomethyl-4-methylsulfonyl benzoic acid with the structure of

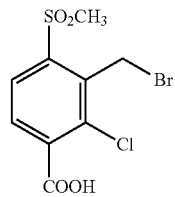 [SMILES: CS(=O)(=O)c1ccc(C(=O)O)c(Cl)c1CBr]

is reacted with a compound of formula (II) to prepare a compound of formula (III), (2) the compound of formula (III) is reacted with a compound of formula (IV) to obtain a compound of formula (V), and (3) the compound of formula (V) is subjected to a rearrangement reaction to afford a compound of formula (I) with hydrogen as $R_3$, wherein, the compound of formula (II) is shown as follows:

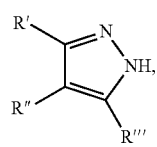

wherein, R', R", and R'" represent hydrogen, C1-C4 alkyl, C1-C4 halogenated alkyl, or halogen, R', R", and R'" are the same or different;

the compound of formula (III) is shown as follows:

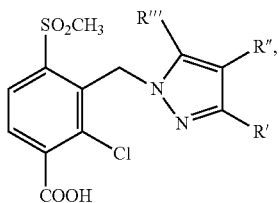
(III)

wherein, R', R", and R'" represent hydrogen, C1-C4 alkyl, C1-C4 halogenated alkyl, or halogen, R', R", and R'" are the same or different;
the compound of formula (IV) is shown as follows:

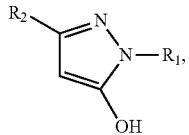
(IV)

wherein $R_1$ represents C1-C3 alkyl, and $R_2$ represents hydrogen or C1-C4 alkyl; and
the compound of formula (V) is shown as follows:

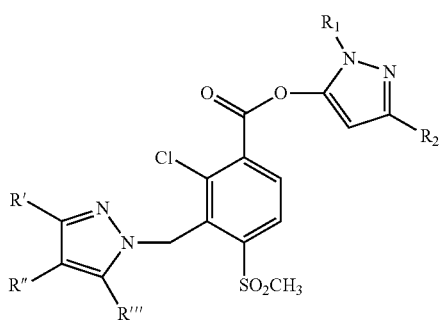
(V)

wherein, R', R", and R'" represent hydrogen, C1-C4 alkyl, C1-C4 halogenated alkyl, or halogen, R', R", and R'" are the same or different, $R_1$ represents C1-C3 alkyl, and $R_2$ represents hydrogen or C1-C4 alkyl.

3. The method according to claim 2, wherein step (1) is conducted in the presence of a solvent and an alkali, at a reaction temperature of 0-10° C., for 1-12 hours, wherein, the solvent is acetonitrile or DMF, and the alkali is sodium hydride.

4. The method according to claim 2, wherein step (2) is conducted in the presence of a solvent and a deacid reagent, at a reaction temperature of 0-10° C., for 1-6 hours, wherein, the solvent is 1,2-dichloroethane, and the deacid reagent is triethylamine.

5. The method according to claim 2, wherein step (3) is conducted in the presence of a solvent and a catalyst, at a reaction temperature of 40-60° C., for 1-6 hours, wherein, the solvent is 1,2-dichloroethane, and the catalyst is acetone cyanohydrin.

6. The method according to claim 2, further comprises step (4): a compound of formula (I) with hydrogen as $R_3$ is reacted with a compound of formula (VI) to obtain a compound of formula (I) with a non-hydrogen group as $R_3$, the compound of formula (VI) is shown as follows:

$$Y—R_3 \qquad (VI)$$

wherein, in formula VI, $R_3$ represents C1-C6 alkyl carbonyl, C1-C6 alkoxyl carbonyl, C1-C6 alkoxyl carbonyl methyl, C1-C4 alkyl sulfonyl, phenylsulfonyl substituted by alkyl, or benzoyl, and Y represents halogen.

7. The method according to claim 6, wherein step (4) is conducted in the presence of a solvent and a deacid reagent, at a reaction temperature of 0-20° C., for 0.5-3 hours; wherein, the solvent is acetonitrile or dichloromethane, and the deacid reagent is triethylamine or potassium carbonate.

8. A herbicidal composition, which comprises a herbicidally effective amount of at least one pyrazole compound or the salt thereof according to claim 1.

9. The herbicidal composition according to claim 8, which also comprises a preparation auxiliary.

10. A method for controlling a harmful plant, comprising a step of applying a herbicidally effective amount of the herbicidal composition according to claim 8 to the plant or an area with the harmful plant.

11. A method for controlling a harmful plant growing in a desirable crop, comprising a step of applying a herbicidally effective amount the herbicidal composition according to claim 8 to the plant or an area with the harmful plant.

12. The method according to claim 11, wherein the desirable crop is a genetically modified crop or a crop treated by a genome editing technique.

13. A method for controlling a harmful plant, which comprises a step of applying a herbicidally effective amount of at least one pyrazole compound or the salt thereof according to claim 1 to the plant or an area with the plant.

14. A method for controlling a harmful plant growing in a desirable crop, comprising a step of applying a herbicidally effective amount of at least one pyrazole compound or the salt thereof according to claim 1 to the plant or an area with the harmful plant.

15. The method according to claim 14, wherein the desirable crop is a genetically modified crop or a crop treated by a genome editing technique.

16. A pyrazole compound or a salt thereof,

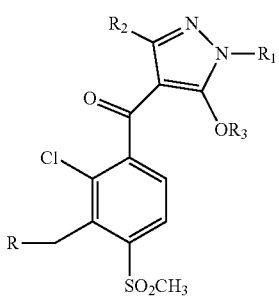
(I)

wherein
R represent

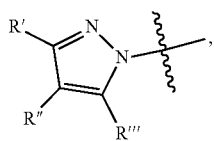

R', R", and R'" represent hydrogen, methyl, fluoro methyl or chlorine, wherein, R', R", and R'" are the same or different;
$R_1$ represents methyl, ethyl or isopropyl;
$R_2$ represents hydrogen, methyl, ethyl or cyclopropyl; and
$R_3$ represents hydrogen, C1-C6 alkyl carbonyl, C1-C6 alkoxyl carbonyl, C1-C6 alkoxyl carbonyl methyl, C1-C4 alkyl sulfonyl, phenylsulfonyl substituted by alkyl, or benzoyl.

17. A method for controlling a harmful plant growing in a desirable crop, comprising a step of applying a herbicidally effective amount of at least one pyrazole compound or the salt thereof according to claim 16 the plant or an area with the harmful plant.

18. A pyrazole compound or a salt thereof, wherein the compound is selected from

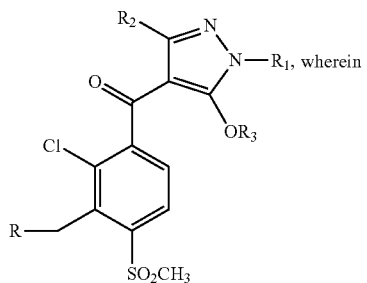

(I)

| Serial NO. | $R_1$ | $R_2$ | $R_3$ | R |
|---|---|---|---|---|
| 01 | —CH₃ | —CH₃ | —H | 4-methyl-1-methylpyrazole |
| 02 | —CH₃ | —CH₃ | —H | 1-methylpyrazole |
| 03 | —CH₃ | —CH₃ | —H | 3-methyl-1-methylpyrazole |
| 04 | —CH₃ | —CH₃ | —H | 3,5-dimethyl-1-methylpyrazole |
| 05 | —CH₃ | —CH₂CH₃ | —H | 4-chloro-1-methylpyrazole |
| 06 | —CH₃ | —CH₂CH₃ | —H | 1-methylpyrazole |

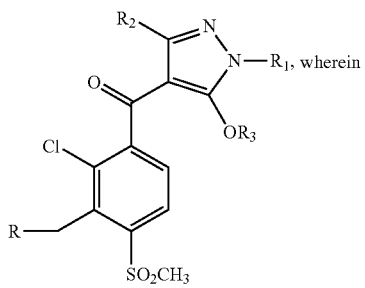
(I)
| Serial NO. | R₁ | R₂ | R₃ | R |
|---|---|---|---|---|
| 07 | —CH₃ | —H | —H | 4-methyl-1-methyl-pyrazole |
| 08 | —CH₃ | —H | —H | 3-methyl-1-methyl-pyrazole |
| 09 | —CH₃ | —H | —H | 3,5-dimethyl-1-methyl-pyrazole |
| 10 | —CH₃ | —H | —H | 4-chloro-1-methyl-pyrazole |
| 11 | —CH₃ | cyclopropyl | —H | 4-chloro-1-methyl-pyrazole |
| 12 | —CH₃ | cyclopropyl | —H | 4-methyl-1-methyl-pyrazole |
| 13 | —CH₃ | cyclopropyl | —H | 3,5-dimethyl-1-methyl-pyrazole |

-continued
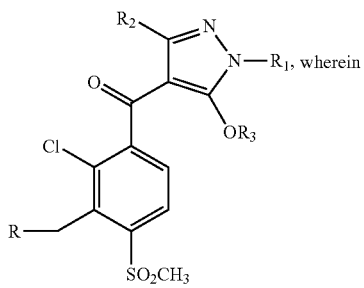
(I)
| Serial NO. | R₁ | R₂ | R₃ | R |
|---|---|---|---|---|
| 14 | —CH₃ | cyclopropyl | —H | 1H-pyrazol-1-yl |
| 15 | —CH₂CH₃ | —CH₃ | —H | 1H-pyrazol-1-yl |
| 16 | —CH₂CH₃ | —CH₃ | —H | 4-methyl-1H-pyrazol-1-yl |
| 17 | —CH₂CH₃ | —CH₃ | —H | 3,5-dimethyl-1H-pyrazol-1-yl |
| 18 | —CH₂CH₃ | —H | —H | 1H-pyrazol-1-yl |
| 19 | —CH₂CH₃ | —H | —H | 4-methyl-1H-pyrazol-1-yl |
| 20 | —CH₂CH₃ | —H | —H | 3,5-dimethyl-1H-pyrazol-1-yl |
| 21 | —CH₂CH₃ | cyclopropyl | —H | 1H-pyrazol-1-yl |

-continued (I)

[Structure of formula (I): pyrazole ring with R2 at 3-position, N-R1, OR3, connected via C=O to phenyl ring bearing Cl, CH2R, and SO2CH3]

| Serial NO. | R₁ | R₂ | R₃ | R |
|---|---|---|---|---|
| 22 | —CH₂CH₃ | cyclopropyl | —H | 4-methyl-1-methyl-pyrazol-yl (H₃C on 4-position, N–CH₃) |
| 23 | —CH₂CH₃ | cyclopropyl | —H | 3,5-dimethyl-1-methyl-pyrazol-yl |
| 24 | —CH₂CH₃ | —CH₂CH₃ | —H | 1-methyl-pyrazol-yl |
| 25 | —CH₂CH₃ | —CH₂CH₃ | —H | 4-methyl-1-methyl-pyrazol-yl |
| 26 | —CH₂CH₃ | —CH₂CH₃ | —H | 3,5-dimethyl-1-methyl-pyrazol-yl |
| 27 | —CH(CH₃)₂ (isopropyl) | cyclopropyl | —H | 1-methyl-pyrazol-yl |
| 28 | —CH(CH₃)₂ (isopropyl) | —H | —H | 4-methyl-1-methyl-pyrazol-yl |

-continued

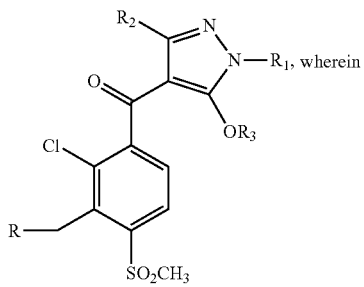

| Serial NO. | R₁ | R₂ | R₃ | R |
|---|---|---|---|---|
| 29 | $-CH(CH_3)_2$ (isobutyl shown as H₃C-CH-CH₃) | $-CH_2CH_3$ | $-H$ | 3,5-dimethyl-1-methyl-pyrazol-4-yl |
| 30 | isobutyl | $-CH_3$ | $-H$ | 4-chloro-1-methyl-pyrazol-3-yl |
| 31 | $-CH_3$ | $-CH_3$ | $-C(O)OCH_2CH_3$ | 4-methyl-1-methyl-pyrazol-3-yl |
| 32 | $-CH_3$ | $-CH_3$ | $-S(O)_2CH_2CH_3$ | 4-methyl-1-methyl-pyrazol-3-yl |
| 33 | $-CH_3$ | $-CH_3$ | $-S(O)_2-C_6H_4-CH_3$ (tosyl) | 3,5-dimethyl-1-methyl-pyrazol-4-yl |
| 34 | $-CH_3$ | $-CH_3$ | $-C(O)C_6H_5$ | 3,5-dimethyl-1-methyl-pyrazol-4-yl |
| 35 | $-CH_3$ | $-CH_3$ | $-C(CH_3)_2-O-C(O)-CH_2CH_3$ | 3,5-dimethyl-1-methyl-pyrazol-4-yl |

-continued

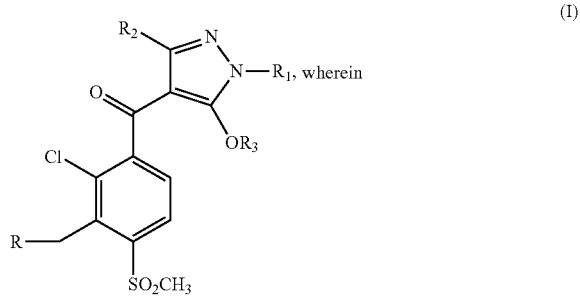

(I)

| Serial NO. | R₁ | R₂ | R₃ | R |
|---|---|---|---|---|
| 36 | —CH₃ | —CH₃ | ethyl propionate ester group (—O—C(=O)—CH₂CH₃ via O-CH₂CH₃) | 3,5-dimethyl-1-methylpyrazolyl |
| 39 | —CH₃ | —CH₃ | —C(=O)CH₃ | 3,5-dimethyl-1-methylpyrazolyl |
| 40 | —CH₃ | —CH₃ | 3,6-dichloropyridin-2-yl C(=O)— | 3,5-dimethyl-1-methylpyrazolyl |
| 41 | —CH₃ | —CH₃ | —H | 3,5-bis(trifluoromethyl)-1-methylpyrazolyl |

19. A method for controlling a harmful plant growing in a desirable crop, comprising a step of applying a herbicidally effective amount of at least one pyrazole compound or the salt thereof according to claim 18 to the plant or an area with the harmful plant.

* * * * *